US008367687B2

(12) United States Patent
Brain et al.

(10) Patent No.: US 8,367,687 B2
(45) Date of Patent: Feb. 5, 2013

(54) PYRAZOLE DERIVATIVES

(75) Inventors: Christopher Thomas Brain, Cambridge, MA (US); Moo Sung, Cambridge, MA (US); Young Shin Cho, Cambridge, MA (US); Ying Hou, Cambridge, MA (US)

(73) Assignees: Novartis AG, Basel (CH); Astex Therapeutics Ltd., Cambridge (GB)

( * ) Notice: Subject to any disclaimer, the term of this patent is extended or adjusted under 35 U.S.C. 154(b) by 85 days.

(21) Appl. No.: 12/746,265

(22) PCT Filed: Dec. 8, 2008

(86) PCT No.: PCT/EP2008/067037
§ 371 (c)(1),
(2), (4) Date: Jun. 4, 2010

(87) PCT Pub. No.: WO2009/071701
PCT Pub. Date: Jun. 11, 2009

(65) Prior Publication Data
US 2010/0280033 A1 Nov. 4, 2010

Related U.S. Application Data

(60) Provisional application No. 61/012,276, filed on Dec. 7, 2007.

(51) Int. Cl.
*A01N 43/54* (2006.01)
*A61K 31/505* (2006.01)
(52) U.S. Cl. ............... 514/275; 514/341; 546/275.4; 544/295
(58) Field of Classification Search .................. 544/331; 546/275.4
See application file for complete search history.

(56) References Cited

U.S. PATENT DOCUMENTS

| | | | |
|---|---|---|---|
| 6,884,804 B2 | 4/2005 | Choon-Moon | |
| 6,979,686 B1 | 12/2005 | Naraian et al. | |
| 2007/0287737 A1* | 12/2007 | Goutopoulos et al. | 514/342 |
| 2010/0144756 A1* | 6/2010 | Bolea et al. | 514/255.05 |

FOREIGN PATENT DOCUMENTS

| | | |
|---|---|---|
| WO | WO 01/14375 A1 | 3/2001 |
| WO | 0246184 A1 | 6/2002 |
| WO | WO 02/079193 A1 | 10/2002 |
| WO | WO 03/051886 A1 | 6/2003 |
| WO | 2004005282 A1 | 1/2004 |
| WO | 2004035588 A1 | 4/2004 |
| WO | WO 2005103036 A1 * | 11/2005 |
| WO | 2007024843 A2 | 3/2007 |
| WO | 2007132220 A1 | 11/2007 |

OTHER PUBLICATIONS

A.M. Traynor et al., Drugs of Today, 40(8), 697-710, 698 (2004).*
F.F. De Arruda, et al., Int. J. Radiation Oncology Biol. Phys., 64(2), 363-373 (2006).*
A.K. Rustgi, Molecular Biology of the Esophagus and Stomach, in 1 Cancer Principles & Practice of Oncology 989-993, 991 (V.T. DeVita, Jr. et al. eds., 8th ed., 2008).*
B.C. Bastian, Genetic Progression, in From Melanocytes to Melanoma the Progression to Malignancy 197, 201 (V. J. Hearing et al., eds., 2006).*
L. Pusztai, Histopathologic and Molecular Markers of Prognosis and Response to Therapy, in Breast Cancer 324, 326-328.*
S. Cannistra et al, Ovarian Cancer, Fallopian Tube Carcinoma and Peritoneal Carcinoma in, 2 Cancer Principles & Practice of Oncology 1568 (V.T. DeVita, Jr. et al. eds., 8th ed., 2008).*
K. Odunsi et al, Molecular Biology of Gynecological Cancers, in 2 Cancer Principles & Practice of Oncology 1487, 1492 (V.T. DeVita, Jr. et al. eds., 8th ed., 2008).*
S.K. Libutti, Colon Cancer in, 1 Cancer Principles & Practice of Oncology 1232, 1243 (V.T. DeVita, Jr. et al. eds., 8th ed., 2008).*
A. Kamb, Nature Reviews Drug Discovery 2, 161-165 (2005).*
N.F. Smith, Molecular Cancer Therapeutics, 6, 428-440, 428 (2007).*
N.E. Sharpless et al., Nature Reviews Drug Discovery 5, 741-754, 742 (2006).*
C. Abad-Zapatero, Drug Discovery Today, 1-8 (2010).*
K.P. Olive et al., Clinical Cancer Research 12, 5277-5287 (2006).*
Y. Song et al., Cancer a Conceptual Framework in, 1 Cancer Principles & Practice of Oncology 1, 5-6 (V.T. DeVita, Jr. et al. eds., 8th ed., 2008).*
B. Hann et al., Current Opinion in Cell Biology, 13, 778-784 (2001).*
K. G. Chen et al., How Melanoma Cells Evade Chemotherapy, in From Melanocytes to Melanoma the Progression to Malignancy 591 (V. J. Hearing et al., eds., 2006).*
L.I. Zon et al., Nature Reviews Drug Discovery 4, 35 (2005).*
The Condensed Chemical Dictionary 822 (Gessner G. Hawley ed., 9th ed., 1977); Concise Chemical and Technical Dictionary 1081 (H. Bennett ed., 4th ed., 1986); Hawley'S Condensed Chemical Dictionary 1186 (Richard J. Lewis, Sr. ed., 15th ed., 2007).*
C. Pillonel, Pest Management Science, 61, 1069-1076 (2005).*
J.H. Poupaert, Drug Design: Basic Principles and Applications, in 2 Encyclopedia of Pharmaceutical Technology 1362-1369, 1367 (James Swarbrick ed., 3rd ed., 2007).*

* cited by examiner

*Primary Examiner* — James O Wilson
*Assistant Examiner* — Alexander R Pagano
(74) *Attorney, Agent, or Firm* — Laura K. Madden

(57) ABSTRACT

The present application describes organic compounds that are useful for the treatment, prevention and/or amelioration of diseases, particularly pyrazole compounds and derivatives are described which inhibit protein kinases. The organic compounds are useful in treating proliferative disease.

11 Claims, No Drawings

PYRAZOLE DERIVATIVES

This application is a U.S. National Phase filing of International Application Ser. No. PCT/EP2008/1067037 filed 8 Dec. 2008 and claims priority to U.S. Provisional Application Ser. No. 61/1012,276 filed 7 Dec. 2007.

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (Hardie, G. and Hanks, S. The Protein Kinase Facts Book, I and II, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J. 1995, 9, 576-596; Knighton et al., Science 1991, 253, 407-414; Hiles et al., Cell 1992, 70, 419-429; Kunz et al., Cell 1993, 73, 585-596; Garcia-Bustos et al., EMBO J. 1994, 13, 2352-2361).

In general, protein kinases mediate intracellular signaling by affecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor-$\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK1-also known as cdc2, and CDK2), cyclin B1-B3 (CDK1) and cyclin D1-D3 (CDK2, CDK4, CDK5, CDK6), cyclin E (CDK2). Each of these complexes is involved in a particular phase of the cell cycle. Not all members of the CDK family are involved exclusively in cell cycle control, however. Thus CDKs 7, 8, and 9 are implicated in the regulation of transcription, and CDK5 plays a role in neuronal and secretory cell function.

The activity of CDKs is regulated post-translationally, by transitory associations with other proteins, and by alterations of their intracellular localization. Tumor development is closely associated with genetic alteration and deregulation of CDKs and their regulators, suggesting that inhibitors of CDKs may be useful anti-cancer therapeutics. Indeed, early results suggest that transformed and normal cells differ in their requirement for, e.g., cyclin A/CDK2 and that it may be possible to develop novel antineoplastic agents devoid of the general host toxicity observed with conventional cytotoxic and cytostatic drugs. While inhibition of cell cycle-related CDKs is clearly relevant in, e.g., oncology applications, this may not be the case for the inhibition of RNA polymerase-regulating CDKs. On the other hand, inhibition of CDK9/cyclin T function was recently linked to prevention of HIV replication and the discovery of new CDK biology thus continues to open up new therapeutic indications for CDK inhibitors (Sausville, E. A. Trends Molec. Med. 2002, 8, S32-S37).

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. Fischer, P. M. Curr. Opin. Drug Discovery Dev. 2001, 4, 623-634) have been found to possess anti-proliferative properties by virtue of CDK-specific ATP antagonism.

At a molecular level mediation of cdk/cyclin complex activity requires a series of stimulatory and inhibitory phosphorylation, or dephosphorylation, events. Cdk phosphorylation is performed by a group of cdk activating kinases (CAKs) and/or kinases such as wee1, Myt1 and Mik1. Dephosphorylation is performed by phosphatases such as cdc25 (a & c), pp 2a, or KAP.

Cdk/cyclin complex activity may be further regulated by two families of endogenous cellular proteinaceous inhibitors: the Kip/Cip family, or the INK family. The INK proteins specifically bind cdk4 and cdk6. $p16^{ink4}$ (also known as MTS1) is a potential tumour suppressor gene that is mutated, or deleted, in a large number of primary cancers. The Kip/Cip family contains proteins such as $p21^{Cip1,Waf1}$, $p27^{Kip1}$ and $p57^{kip2}$. As discussed previously p21 is induced by p53 and is able to inactivate the cdk2/cyclin(E/A) and cdk4/cyclin(D1/D2/D3) complexes. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of cdks, and their associated proteins, in co-ordinating and driving the cell cycle in proliferating cells have been outlined above. Some of the biochemical pathways in which cdks play a key role have also been described. The development of monotherapies for the treatment of proliferative disorders, such as cancers, using therapeutics targeted generically at cdks, or at specific cdks, is therefore potentially highly desirable. Cdk inhibitors could conceivably also be used to treat other conditions such as viral infections, autoimmune diseases and neuro-degenerative diseases, amongst others. Cdk targeted therapeutics may also provide clinical benefits in the treatment of the previously described diseases when used in combination therapy with either existing, or new, therapeutic agents. Cdk targeted anticancer therapies could potentially have advantages over many current antitumour agents as they would not directly interact with DNA and should therefore reduce the risk of secondary tumour development.

Thus, there is a continued need to find new therapeutic agents to treat human diseases. Accordingly, there is a great need to develop inhibitors of protein kinases, such as CDK1, CDK2, CDK4, CDK5, CDK6, CDK7, CDK8 and CDK9.

SUMMARY OF THE INVENTION

There remains a need for new treatments and therapies for protein kinase-associated disorders. There is also a need for compounds useful in the treatment or prevention or amelioration of one or more symptoms of cancer, transplant rejections, and autoimmune diseases. Furthermore, there is a need for methods for modulating the activity of protein kinases, such as CDK1, CDK2, CDK4, CDK5, CDK6, CDK7, CDK8 and CDK9, using the compounds provided herein. In one aspect, the invention provides a compound of Formula Ia:

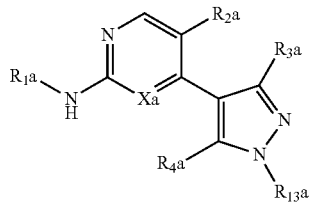

(Ia)

where $R^{1a}$ is H, alkyl, alkenyl, alkynyl, aryl, cycloalkyl, alkylaryl, alkoxy, alkylcycloalkyl, hydroxyl, het, alkylhet, arylcycloalkyl, hetcycloalkyl, $C_{(0-6)}R^{11a}R^{12a}$, cycloalkylaryl, or cycloalkylhet, which may be unsubstituted or substituted;

$R^{2a}$ is H, alkyl, alkenyl, alkynyl, hydroxyl, halo, CN, $CONH_2$, alkyl, or cycloalkyl, which may be unsubstituted or substituted;

$R^{3a}$ is H, alkyl, alkenyl, alkynyl, cycloalkyl, het, hydroxyl, halo, CN, CHO, $OR^{7a}$, $NHR^{7a}$, $NHSO_2R^{7a}$, $NHCONHR^{7a}$, $NHCOOR^{7a}$, $CH_2OR^{7a}$, $CONR^{8a}R^{9a}$, which may be unsubstituted or substituted;

$R^{7a}$, $R^{8a}$, and $R^{9a}$ independently are hydrogen, alkyl, alkenyl, alkynyl, cycloalkyl, het, aryl, which may be unsubstituted or substituted;

Xa is N or $CR^{10a}$ where $R^{10a}$ is H, halogen, alkyl, alkenyl, or alkynyl;

$R^{4a}$ is H, alkyl, alkenyl, alkynyl, cycloalkyl, het, or halo, which may be unsubstituted or substituted;

$R^{13a}$ is H, alkyl, alkenyl, alkynyl, cycloalkyl, or $C_{(0-6)}R^{11a}R^{12a}$ which may be unsubstituted or substituted, $R^{11a}$ and $R^{12a}$ are independently H, a bond, $NH_{(0-2)}$, —O—, hydroxyl, aryl, alkyl, alkenyl, alkynyl, $C(O)C_{(0-6)}$, alkoxy, halo, cycloalkyl, het, $C(O)OC_{(0-6)}$, CN which may be unsubstituted or substituted;

het is a 5-7 membered monocyclic heterocyclic ring which may be aromatic or non-aromatic, containing 1-4 heteroring atoms selected from N, O, and S; or an 8-12 membered fused ring system that includes one 5-7 membered heterocyclic ring which may be aromatic or non-aromatic, containing 1, 2, or 3 heteroring atoms selected from N, O and S, which het is unsubstituted or substituted; and $R^{1a}$, $R^{2a}$, $R^{3a}$, $R^{4a}$, $R^{7a}$, $R^{8a}$, $R^{9a}$, $R^{11a}$, $R^{12a}$, and $R^{13a}$ may be substituted with one or more of alkyl, alkenyl, alkynyl, alkylaryl, cycloalkyl, halo, alkoxy, het, aryl, alkylaryl, hydroxyl, $CF_3$, COOalkyl, $CR^{3a}$, and carbonyl.

In another aspect, the present invention provides a compound of Formula I:

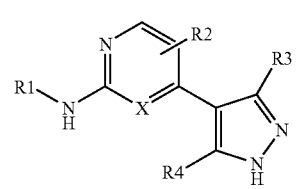

(I)

or a pharmaceutically acceptable salt, wherein $R^1$ is $C_{1-6}$-alkyl, $C_{3-14}$-cycloalkyl, a 3-14 membered cycloheteroalkyl group, $C_{6-14}$aryl, $C_{1-6}$-alkoxy, $C_{1-6}$alkyC$_{6-14}$aryl, $C_{1-6}$alkylC$_{3-14}$cycloalkyl, $C_{1-6}$alkyl-3-14 membered cycloheteroalkyl group, $C_{1-6}$alkyl-5-14 membered heteroaryl group, $C_{1-6}$alkylOR$^7$, $C_{1-6}$alkylNR$^5$R$^6$, $C_{1-6}$alkoxyC$_{6-14}$aryl, $C_{1-6}$alkylCN, or $C_{1-6}$alkylC(O)OR$^7$, which may be unsubstituted or substituted with one or more of $C_{1-6}$-alkyl, $C_{6-14}$-aryl, hydroxyl, $C_{1-6}$-alkylhalo, $C_{1-6}$alkoxyhalo, halo, $C_{1-6}$-alkoxy, $C_{1-6}$alkyC$_{6-14}$aryl, C(O)OR$^8$, CN, oxo, or NR$^9$R$^{10}$;

$R^2$ is H, $C_{1-6}$-alkyl, $C_{2-6}$-alkenyl, $C_{2-6}$-alkynyl, hydroxyl, or halo;

$R^3$ and $R^4$ are independently H, $C_{1-6}$-alkyl, $C_{3-14}$-cycloalkyl, or halo, which may be unsubstituted or substituted;

$R^5$, $R^6$, $R^7$, $R^8$, $R^9$, and $R^{10}$ independently are hydrogen, $C_{1-6}$-alkyl, $C_{2-6}$-alkenyl, $C_{2-6}$-alkynyl, $C_{3-14}$-cycloalkyl, a 5-14 membered heteroaryl group, $C_{6-14}$-aryl, C(O)OR$^{11}$, or C(O)R$^{11}$, which may be unsubstituted or substituted;

X is N or $CR^{12}$ where $R^{11}$ and $R^{12}$ are independently H, halogen, or $C_{1-6}$-alkyl.

In one aspect of the invention, the protein kinase is a protein tyrosine kinase. In one embodiment, the protein kinase is selected from the group consisting of abl, ATK, ber-abl, Blk, Brk, Btk, c-fms, e-kit, c-met, c-src, CDK, cRafl, CSFIR, CSK, EGFR, ErbB2, ErbB3, ErbB4, ERK, Fak, fes, FGFRl, 25 FGFR2, FGFR3, FGFR4, FGFR5, Fgr, FLK-4, flt-1, Fps, Frk, Fyn, GSK, Gst-FlkI, Hck, Her-2, Her-4, IGF-IR, INS-R, Jak, JNK, KDR, Lck, Lyn, MEK, p38, PANHER, PDGFR, PLK, PKC, PYK2, Raf, Rho, ros, SRC, t'ell t'e2, TRK, TYK2, UL97, VEGFR, Yes, and Zap70. In another embodiment, the protein kinase is selected from the group consisting of CDK1, CDK2, CDK4, CDK5, CDK6, CDK7, CDK8 and CDK9. In yet another embodiment, the protein kinase is CDK4.

In another aspect of the invention, the protein kinase is in a cell culture. In still another aspect, the protein kinase is in a mammal.

In another aspect, the invention provides a method of treating a protein kinase-associated disorder, wherein the method includes administering to a subject in need thereof a pharmaceutically acceptable amount of a compound of the Formula I, such that the protein kinase-associated disorder is treated. In one embodiment, the protein kinase is selected from the group consisting of CDK1, CDK2, CDK4, CDK5, CDK6, CDK7, CDK8, and CDK9. In a particular embodiment, the protein kinase is CDK4.

In another aspect, the invention provides a method of treating a serine theronine kinase-associated disorder, wherein the method includes administering to a subject in need thereof a pharmaceutically acceptable amount of a compound of the Formula I, such that the serine theronine kinase-associated disorder is treated. In one embodiment, the disorder is selected from the group consisting of CDK1, CDK2, CDK4, CDK5, CDK6, CDK7, CDK8, and CDK9. In a particular embodiment, the protein kinase is CDK4.

In another embodiment, the protein kinase-associated disorder is selected from the group consisting of blood vessel proliferative disorders, fibrotic disorders, mesangial cell proliferative disorders, metabolic disorders, allergies, asthma, thrombosis, nervous system diseases and cancer.

In another embodiment, the protein kinase-associated disorder is cancer. In yet another embodiment, the cancer is selected from the group consisting of breast, stomach, ovary, colon, lung, brain, larynx, lymphatic system, genitourinary tract (including bladder and prostate), ovarian, gastric, bone, and pancreatic cancer.

In another embodiment, the protein kinase-associated disorder is selected from the group consisting of organ transplant rejection, xeno transplantation, lupus, multiple sclerosis, rheumatoid arthritis, psoriasis, Type 1 diabetes and complications from diabetes, cancer, asthma, atopic dermatitis, autoimmune thyroid disorders, ulcerative colitis, Crohn's disease, Alzheimer's disease and leukemia.

In still another embodiment, the disease is selected from an immune response, an autoimmune disease, a neurodegenerative disease, or a solid or hematologic malignancy. In yet another embodiment, the disease is selected from an allergic or type I hypersensitivity reaction, asthma, graft versus host disease, rheumatoid arthritis, amyotrophic lateral sclerosis, multiple sclerosis, Familial amyotrophic lateral sclerosis, leukemia, or lymphoma In another aspect, the invention provides a method of treating an autoimmune disease, wherein the treatment includes administering to a subject in need thereof a pharmaceutically acceptable amount of a compound of the Formula I, such that the autoimmune disease is treated. In one embodiment, the autoimmune disease is selected from the group consisting of autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis, multiple sclerosis, neuritis, uveitis ophthalmia, polyendocrinopathies, purpura, Reiter's Disease, Stiff-Man Syndrome, autoimmune pulmonary inflammation, autism, Guillain-Barre Syndrome, insulin dependent diabetes mellitis, autoimmune inflammatory eye, autoimmune thyroiditis, hypothyroidism, systemic lupus erhythematosus, Goodpasture's syndrome, Pemphigus, Receptor autoimmunities, autoimmune hemolytic anemia, autoimmune thrombocytopenic purpura, rheumatoid arthritis, mixed connective tissue disease, polymyositis/dermatomyositis, pernicious anemia, idiopathic Addison's disease, infertility, glomerulonephritis, bullous pemphigoid, Sjogren's syndrome, diabetes millitus, adrenergic drug resistance, chronic active hepatitis, primary biliary cirrhosis, vitiligo, vasculitis, post-MI, cardiotomy syndrome, urticaria, atopic dermatitis, asthma, inflammatory myopathies, chronic active hepatitis, primary biliary cirrhosis and T-cell mediated hypersensitivity diseases.

In another aspect, the invention provides a method of treating cancer, wherein the method includes administering to a subject in need thereof a pharmaceutically acceptable amount of a compound of the Formula I such that the cancer disease or disorder is treated. In one embodiment, the cancer is selected from the group consisting of bladder, head and neck, breast, stomach, ovary, colon, lung, brain, larynx, lymphatic system, genitourinary tract, gastrointestinal, ovarian, prostate, gastric, bone, small-cell lung, glioma, colorectal and pancreatic cancer.

In another aspect of the invention, the Formula I or salt thereof is administered, simultaneously or sequentially, with an antiinflammatory, antiproliferative, chemotherapeutic agent, immunosuppressant, anti-cancer, cytotoxic agent or kinase inhibitor other than a compound of the Formula I or salt thereof. In one embodiment, the compound of the Formula I or salt thereof is administered, simultaneously or sequentially, with one or more of a PTK inhibitor, cyclosporin A, CTLA4-Ig, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal antiinflammatory drugs, steroids, gold compounds, antiproliferative agents, FK506, mycophenolate mofetil, cytotoxic drugs, TNF-α inhibitors, anti-TNF antibodies or soluble TNF receptor, rapamycin, leflunimide, cyclooxygenase-2 inhibitors, paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

In another aspect, the invention provides a packaged protein kinase-associated disorder treatment, wherein the treatment includes a protein kinase-modulating compound of the Formula I, packaged with instructions for using an effective amount of the protein kinase-modulating compound to treat a protein kinase-associated disorder.

DETAILED DESCRIPTION OF THE INVENTION

This invention is directed to compounds, e.g., pyrazolyl pyridine and pyrazolyl pyrimidine compounds, and intermediates thereto, as well as pharmaceutical compositions containing the compounds for use in treatment of protein kinase-associated disorders. This invention is also directed to the compounds of the invention or compositions thereof as modulators of Jak1, Jak2 and Jak3, as well as CDK1, CDK2, CDK4, CDK5, CDK6, CDK7, CDK8 and CDK9. The present invention is also directed to methods of combination therapy for inhibiting protein kinase activity in cells, or for treating, preventing or ameliorating of one or more symptoms of cancer, transplant rejections, and autoimmune diseases in patients using the compounds of the invention or pharmaceutical compositions, or kits thereof.

In one aspect, the invention provides compounds of the Formula Ia:

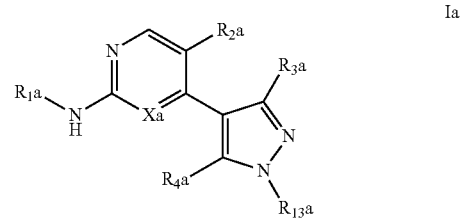

where $R^{1a}$ is H, alkyl, alkenyl, alkynyl, aryl, cycloalkyl, alkylaryl, alkoxy, alkylcycloalkyl, hydroxyl, het, alkylhet, arylcycloalkyl, hetcycloalkyl, $C_{(0-6)}R^{11a}R^{12a}$, cycloalkylaryl, or cycloalkylhet, which may be unsubstituted or substituted;

$R^{2a}$ is H, alkyl, alkenyl, alkynyl, hydroxyl, halo, CN, $CONH_2$, alkyl, or cycloalkyl, which may be unsubstituted or substituted;

$R^{3a}$ is H, alkyl, alkenyl, alkynyl, cycloalkyl, het, hydroxyl, halo, CN, CHO, $OR^{7a}$, $NHR^{7a}$, $NHSO_2R^{7a}$, $NHCONHR^{7a}$, $NHCOOR^{7a}$, $CH_2OR^{7a}$, $CONR^{8a}R^{9a}$, which may be unsubstituted or substituted;

$R^{7a}$, $R^{8a}$, and $R^{9a}$ independently are hydrogen, alkyl, alkenyl, alkynyl, cycloalkyl, het, aryl, which may be unsubstituted or substituted;

Xa is N or $CR^{10a}$ where $R^{10a}$ is H, halogen, alkyl, alkenyl, or alkynyl;

$R^{4a}$ is H, alkyl, alkenyl, alkynyl, cycloalkyl, het, or halo, which may be unsubstituted or substituted;

$R^{13a}$ is H, alkyl, alkenyl, alkynyl, cycloalkyl, or $C_{(0-6)}R^{11a}R^{12a}$ which may be unsubstituted or substituted, $R^{11a}$ and $R^{12a}$ are independently H, a bond, $NH_{(0-2)}$, —O—, hydroxyl, aryl, alkyl, alkenyl, alkynyl, $C(O)C_{(0-6)}$, alkoxy, halo, cycloalkyl, het, $C(O)OC_{(0-6)}$, CN which may be unsubstituted or substituted;

het is a 5-7 membered monocyclic heterocyclic ring which may be aromatic or non-aromatic, containing 1-4 heteroring atoms selected from N, O, and S; or an 8-12 membered fused ring system that includes one 5-7 membered heterocyclic ring which may be aromatic or non-aromatic, containing 1, 2, or 3 heteroring atoms selected from N, O and S, which het is unsubstituted or substituted; and $R^{1a}$, $R^{2a}$, $R^{3a}$, $R^{4a}$, $R^{7a}$, $R^{8a}$, $R^{9a}$, $R^{11a}$, $R^{12a}$, and $R^{13a}$ may be substituted with one or more of alkyl, alkenyl, alkynyl, alkylaryl, cycloalkyl, halo, alkoxy, het, aryl, alkylaryl, hydroxyl, $CF_3$, COOalkyl, $CR^{3a}$, and carbonyl.

In an embodiment, the invention includes the compound of formula (Ia) wherein $R^{1a}$ is het, cycloalkylaryl, alkylaryl, $C_{(0-6)}R^{11a}R^{12a}$, or alkylhet, which may be substituted or unsubstituted, and $R^{13a}$ is H.

In another embodiment, the invention includes the compound of formula (Ia) wherein $R^{1a}$ is het, or cycloalkylaryl, which may be substituted or unsubstituted; $R^{2a}$ is H, halo, or alkyl, in which alkyl may be substituted or unsubstituted; $R^{3a}$ is H, or alkyl in which alkyl may be substituted or unsubstituted; and $R^{4a}$ is alkyl, or cycloalkyl, which may be substituted or unsubstituted.

In a further embodiment, the invention includes a compound of formula Ia wherein $R^{1a}$ is selected from:

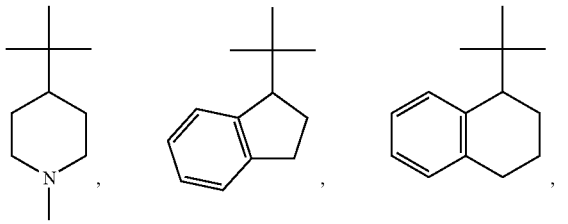

and $R^{3a}$ is methyl or isopropyl.

In another aspect, the invention provides compounds of the Formula I:

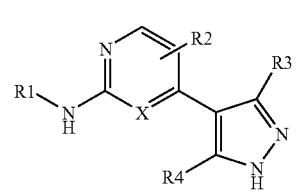

or a pharmaceutically acceptable salt, wherein
$R^1$ is $C_{1-6}$-alkyl, $C_{3-14}$-cycloalkyl, a 3-14 membered cycloheteroalkyl group, $C_{6-14}$aryl, $C_{1-6}$-alkoxy, $C_{1-6}$alkyC$_{6-14}$aryl, $C_{1-6}$alkylC$_{3-14}$cycloalkyl, $C_{1-6}$alkyl-3-14 membered cycloheteroalkyl group, $C_{1-6}$alkyl-5-14 membered heteroaryl group, $C_{1-6}$alkylOR$^7$, $C_{1-6}$alkylNR$^5$R$^6$, $C_{1-6}$alkoxyC$_{6-14}$aryl, $C_{1-6}$alkylCN, or $C_{1-6}$alkylC(O)OR$^7$, which may be unsubstituted or substituted with one or more of $C_{1-6}$-alkyl, $C_{6-14}$-aryl, hydroxyl, $C_{1-6}$-alkylhalo, $C_{1-6}$alkoxyhalo, halo, $C_{1-6}$-alkoxy, $C_{1-6}$alkyC$_{6-14}$aryl, C(O)OR$^8$, CN, oxo, or NR$^9$R$^{10}$;

$R^2$ is H, $C_{1-6}$-alkyl, $C_{2-6}$-alkenyl, $C_{2-6}$-alkynyl, hydroxyl, or halo;

$R^3$ and $R^4$ are independently H, $C_{1-6}$-alkyl, $C_{3-14}$-cycloalkyl, or halo, which may be unsubstituted or substituted;

$R^5$, $R^6$, $R^7$, $R^8$, $R^9$, and $R^{10}$ independently are hydrogen, $C_{1-6}$-alkyl, $C_{2-6}$-alkenyl, $C_{2-6}$-alkynyl, $C_{3-14}$-cycloalkyl, a 5-14 membered heteroaryl group, $C_{6-14}$-aryl, C(O)OR$^{11}$, or C(O)R$^{11}$, which may be unsubstituted or substituted;

X is N or $CR^{12}$ where $R^{11}$ and $R^{12}$ are independently H, halogen, or $C_{1-6}$-alkyl.

In a further embodiment, the invention includes a compound of formula I wherein $R^1$ is $C_{1-6}$-alkyl, $C_{3-14}$-cycloalkyl, $C_{6-14}$aryl, a 3-14 membered cycloheteroalkyl group, $C_{1-6}$alkyC$_{6-14}$aryl, $C_{1-6}$alkylC$_{3-14}$cycloalkyl, $C_{1-6}$alkyl-3-14 membered cycloheteroalkyl group, or $C_{1-6}$alkyl-5-14 membered heteroaryl group, which may be unsubstituted or substituted with one or more of $C_{1-6}$-alkyl, $C_{6-14}$-aryl, hydroxyl, $C_{1-6}$-alkylhalo, halo, $C_{1-6}$-alkoxy, $C_{1-6}$alkyC$_{6-14}$aryl.

In another preferred embodiment of the compounds of formula I, $R^1$ is $C_{3-14}$-cycloalkyl, $C_{6-14}$aryl, a 3-14 membered cycloheteroalkyl group, $C_{1-6}$alkyC$_{6-14}$aryl, or $C_{1-6}$alkyl $C_{3-14}$cycloalkyl, which may be unsubstituted or substituted with one or more of $C_{1-6}$-alkyl or $C_{6-14}$-aryl.

In a further embodiment, the invention includes a compound of formula Ia wherein $R^1$ is selected from:

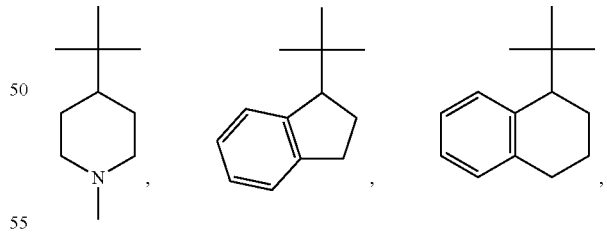

and $R^3$ is methyl or isopropyl.

In another preferred embodiment of the compounds of formula I, $R^3$ and $R^4$ are independently H, $C_{1-6}$-alkyl, or $C_{3-14}$-cycloalkyl.

In another preferred embodiment of the compounds of formula I, one of $R^3$ and $R^4$ is H and the other of $R^3$ and $R^4$ is $C_{1-6}$-alkyl, or $C_{3-14}$-cycloalkyl.

In another preferred embodiment of the compounds of formula I, $R^4$ is H and $R^3$ is methyl, ethyl, or propyl. In another preferred embodiment, $R^3$ is isopropyl.

It is recognized that references to formula I are also intended to refer to formula Ia, and references to formula Ia are also intended to refer to formula I.

In another preferred embodiment of the compounds of formula I, X is N or CH. In another preferred embodiment of the compounds of formula I, X is N.

In another embodiment, the invention includes a pharmaceutical composition comprising a therapeutically effective amount of a compound of formula I or Ia.

In another embodiment, the present invention includes compounds of formula I or Ia in medicine, particularly cancer.

In another embodiment, the invention includes a method of treating a mammal suffering from a proliferative disease which comprises administering to said mammal in need of treatment a therapeutically effective amount of a compound of formula I or Ia. In yet another embodiment, the invention includes a method of inhibiting cell proliferation comprising administering an effective amount of the compound of formula I or Ia to inhibit cell proliferation to a cell or mammal in need thereof.

In certain embodiments, the compound of the present invention is further characterized as a modulator of a protein kinase, including, but not limited to, protein kinases selected from the group consisting of abl, ATK, ber-abl, Blk, Brk, Btk, c-fms, e-kit, c-met, c-src, CDK, cRafl, CSFIR, CSK, EGFR, ErbB2, ErbB3, ErbB4, ERK, Fak, fes, FGFRI, 25 FGFR2, FGFR3, FGFR4, FGFR5, Fgr, FLK-4, flt-1, Fps, Frk, Fyn, GSK, Gst-FlkI, Hck, Her-2, Her-4, IGF-IR, INS-R, Jak, JNK, KDR, Lck, Lyn, MEK, p38, PANHER, PDGFR, PLK, PKC, PYK2, Raf, Rho, ros, SRC, t'ell t'e2, TRK, TYK2, UL97, VEGFR, Yes, and Zap70.

In a preferred embodiment, the protein kinase is selected from the group consisting of CDK1, CDK2, CDK4, CDK5, CDK6, CDK7, CDK8 and CDK9. In another preferred embodiment, the protein kinase is selected from the group consisting of Jak1, Jak2 and Jak3. In a particularly preferred embodiment, the protein kinase is selected from the group consisting of Jak3 and CDK4. In other embodiments, the compounds of the present invention are used for the treatment of protein kinase-associated disorders. As used herein, the term "protein kinase-associated disorder" includes disorders and states (e.g., a disease state) that are associated with the activity of a protein kinase, e.g., CDK4 and Jak3. Non-limiting examples of a protein kinase-associated disorder include blood vessel proliferative disorders, fibrotic disorders, mesangial cell proliferative disorders, metabolic disorders, allergies, asthma, thrombosis, nervous system diseases, organ transplant rejection, autoimmune diseases, and cancer. In another embodiment, the compound of the present invention is further characterized as a modulator of a combination of protein kinases, e.g., Jak3 and CDK4.

In certain embodiments, a compound of the present invention is used for protein kinase-associated diseases, and use of the compound of the present invention as an inhibitor of any one or more protein kinases. It is envisioned that a use can be a treatment of inhibiting one or more isoforms of protein kinases.

The compounds of the invention are inhibitors of cyclin-dependent kinase enzymes (CDKs). Without being bound by theory, inhibition of the CDK4/cyclin D1 complex blocks phosphorylation of the Rb/inactive E2F complex, thereby preventing release of activated E2F and ultimately blocking E2F-dependent DNA transcription. This has the effect of inducing $G_1$ cell cycle arrest. In particular, the CDK4 pathway has been shown to have tumor-specific deregulation and cytotoxic effects.

Furthermore, the compounds of this invention have the potential to block the expansion of auto- or alloreactive T cells, and thus have beneficial effects on autoimmune diseases, as well as transplant rejections.

The present invention includes treatment of one or more symptoms of cancer, transplant rejections, and autoimmune diseases, as well as protein kinase-associated disorders, as described above, but the invention is not intended to be limited to the manner by which the compound performs its intended function of treatment of a disease. The present invention includes treatment of diseases described herein in any manner that allows treatment to occur, e.g., cancer, transplant rejections, and autoimmune diseases.

In certain embodiments, the invention provides a pharmaceutical composition of any of the compounds of the present invention. In a related embodiment, the invention provides a pharmaceutical composition of any of the compounds of the present invention and a pharmaceutically acceptable carrier or excipient of any of these compounds. In certain embodiments, the invention includes the compounds as novel chemical entities.

In one embodiment, the invention includes a packaged protein kinase-associated disorder treatment. The packaged treatment includes a compound of the invention packaged with instructions for using an effective amount of the compound of the invention for an intended use.

The compounds of the present invention are suitable as active agents in pharmaceutical compositions that are efficacious particularly for treating protein kinase-associated disorders, e.g., cancer, transplant rejections, and autoimmune diseases. The pharmaceutical composition in various embodiments has a pharmaceutically effective amount of the present active agent along with other pharmaceutically acceptable excipients, carriers, fillers, diluents and the like. The phrase, "pharmaceutically effective amount" as used herein indicates an amount necessary to administer to a host, or to a cell, issue, or organ of a host, to achieve a therapeutic result, especially the regulating, modulating, or inhibiting protein kinase activity, e.g., inhibition of the activity of a protein kinase, or treatment of cancer, transplant rejections, or autoimmune diseases.

In other embodiments, the present invention provides a method for inhibiting the activity of a protein kinase. The method includes contacting a cell with any of the compounds of the present invention. In a related embodiment, the method further provides that the compound is present in an amount effective to selectively inhibit the activity of a protein kinase.

In other embodiments, the present invention provides a use of any of the compounds of the invention for manufacture of a medicament to treat cancer, transplant rejections, or autoimmune diseases in a subject.

In other embodiments, the invention provides a method of manufacture of a medicament, including formulating any of the compounds of the present invention for treatment of a subject.

Definitions

The term "treat," "treated," "treating" or "treatment" includes the diminishment or alleviation of at least one symptom associated or caused by the state, disorder or disease being treated. In certain embodiments, the treatment comprises the induction of a protein kinase-associated disorder, followed by the activation of the compound of the invention, which would in turn diminish or alleviate at least one symptom associated or caused by the protein kinase-associated disorder being treated. For example, treatment can be diminishment of one or several symptoms of a disorder or complete eradication of a disorder.

The term "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, transplant rejections, and autoimmune diseases, and for other diseases or conditions described herein. In another embodiment, the subject is a cell.

The language "protein kinase-modulating compound," "modulator of protein kinase" or "protein kinase inhibitor" refers to compounds that modulate, e.g., inhibit, or otherwise alter, the activity of a protein kinase. Examples of protein kinase-modulating compounds include compounds of Formula I, as well as Tables 1 and 2, and other examples as described herein (including pharmaceutically acceptable salts thereof, as well as enantiomers, stereoisomers, rotamers, tautomers, diastereomers, atropisomers or racemates thereof).

Additionally, a method of the invention includes administering to a subject an effective amount of a protein kinase-modulating compound of the invention, e.g., protein kinase-modulating compounds of Formula I, as well as Tables 1 and 2, and other examples as described herein (including pharmaceutically acceptable salts thereof, as well as enantiomers, stereoisomers, rotamers, tautomers, diastereomers, atropisomers or racemates thereof).

The term "alkyl" as used herein includes saturated aliphatic groups, including straight-chain alkyl groups (e.g., methyl, ethyl, propyl, hexyl, heptyl, octyl, normyl, decyl, etc.), branched chain alkyl groups (isopropyl, tert-butyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. A cycloalkyl group, as a whole, can have from 3 to 14 ring atoms (e.g., from 3 to 8 carbon atoms for a monocyclic cycloalkyl group and from 7 to 14 carbon atoms for a polycyclic cycloalkyl group). Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups optionally can be substituted with up to four groups independently selected from -L'-$R^5$ and -L'-$R^{10}$, where L', $R^5$, and $R^{10}$ are as described herein. For example, cycloalkyl groups can be substituted with one or more oxo groups.

As used herein, "heteroatom" refers to an atom of any element other than carbon or hydrogen and includes, for example, nitrogen, oxygen, sulfur, phosphorus, and selenium.

As used herein, "cycloheteroalkyl" refers to a non-aromatic cycloalkyl group that contains at least one (e.g., one, two, three, four, or five) ring heteroatom selected from O, N, and S, and optionally contains one or more (e.g., one, two, or three) double or triple bonds. A cycloheteroalkyl group, as a whole, can have from 3 to 14 ring atoms and contains from 1 to 5 ring heteroatoms (e.g., from 3-6 ring atoms for a monocyclic cycloheteroalkyl group and from 7 to 14 ring atoms for a polycyclic cycloheteroalkyl group). The cycloheteroalkyl group can be covalently attached to the defined chemical structure at any heteroatom(s) or carbon atom(s) that results in a stable structure. One or more N or S atoms in a cycloheteroalkyl ring may be oxidized (e.g., morpholine N-oxide, thiomorpholine S-oxide, thiomorpholine S,S-dioxide). In some embodiments, nitrogen atoms of cycloheteroalkyl groups can bear a substituent, for example, a -L'-$R^5$ or -L'-$R^{10}$ group, where L', $R^5$, and $R^{10}$ are as described herein. Cycloheteroalkyl groups can also contain one or more oxo groups, such as phthalimidyl, piperidonyl, oxazolidinonyl, 2,4 (1H, 3H)-dioxo-pyrimidinyl, pyridin-2(1H)-onyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothienyl, piperidinyl, piperazinyl, and the like. In some embodiments, cycloheteroalkyl groups optionally can be substituted with up to four groups independently selected from -L-$R^5$ and -L-$R^{10}$, where L', $R^5$, and $R^{10}$ are as described herein.

As used herein, "aryl" refers to an aromatic monocyclic hydrocarbon ring system or a polycyclic ring system where at least one of the rings in the ring system is an aromatic hydrocarbon ring and any other aromatic rings in the ring system include only hydrocarbons. In some embodiments, a monocyclic aryl group can have from 6 to 14 carbon atoms and a polycyclic aryl group can have from 8 to 14 carbon atoms. The aryl group can be covalently attached to the defined chemical structure at any carbon atom(s) that result in a stable structure. In some embodiments, an aryl group can have only aromatic carbocyclic rings, e.g., phenyl, 1-naphthyl, 2-naphthyl, anthracenyl, phenanthrenyl groups, and the like. In other embodiments, an aryl group can be a polycyclic ring system in which at least one aromatic carbocyclic ring is fused (i.e., having a bond in common with) to one or more cycloalkyl or cycloheteroalkyl rings. Examples of such aryl groups include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, each aryl group optionally can be substituted with up to four groups independently selected from -L'-$R^5$ and -L'-$R^{10}$, where L', $R^5$, and $R^{10}$ are as described herein.

As used herein, "heteroaryl" refers to an aromatic monocyclic ring system containing at least one ring heteroatom selected from O, N, and S or a polycyclic ring system where at least one of the rings in the ring system is aromatic and contains at least one ring heteroatom. A heteroaryl group, as a whole, can have from 5 to 14 ring atoms and contain 1-5 ring heteroatoms. In some embodiments, heteroaryl groups can include monocyclic heteroaryl rings fused to one or more aromatic carbocyclic rings, non-aromatic carbocyclic rings, or non-aromatic cycloheteroalkyl rings. The heteroaryl group can be covalently attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5-membered and 6-membered monocyclic and 5-6 bicyclic ring systems shown below:

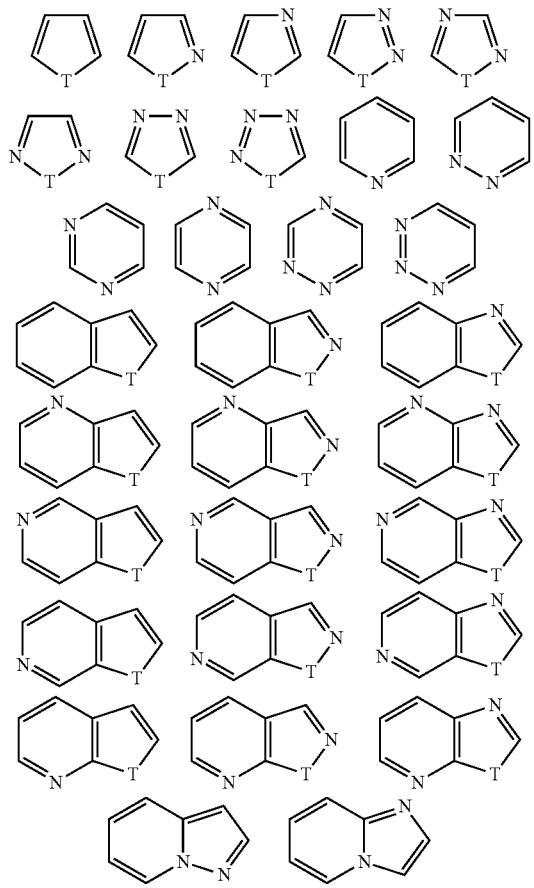

where T is O, S, NH, N-L'-R⁵, or N-L'-R¹⁰, where L', R⁵, and R¹⁰ are as defined herein. Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted with up to four groups independently selected from -L'-R⁵ or -L'-R¹⁰, where L', R⁵, and R¹⁰ are as described herein.

When two substituents together with a commonly bound nitrogen are het, it is understood that the resulting heterocyclic ring is a nitrogen-containing ring, such as aziridine, azetidine, azole, piperidine, piperazine, morphiline, pyrrole, pyrazole, thiazole, oxazole, pyridine, pyrimidine, isoxazole, and the like, wherein such het may be unsubstituted or substituted as defined hereinabove.

"Het" as used herein, refers to heteroaryl and heterocyclic compounds containing at least one S, O or N ring heteroatom. More specifically, "Het" is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S. Examples of het, as used herein, include but are not limited to unsubstituted and substituted pyrrolidyl, tetrahydrofuryl, tetrahydrothiofuryl, piperidyl, piperazyl, purinyl, tetrahydropyranyl, morpholino, 1,3-diazapanyl, 1,4-diazapanyl, 1,4-oxazepanyl, 1,4-oxathiapanyl, furyl, thienyl, pyrryl, pyrrolyl, pyrazolyl, triazolyl, tetrazolyl, indazolyl, oxadiazolyl, imidazolyl, pyrrolidyl, pyrrolidinyl, thiazolyl, oxazolyl, pyridyl, pyrazolyl, pyrazinyl, pyrimidinyl, isoxazolyl, pyrazinyl, quinolyl, isoquinolyl, pyridopyrazinyl, pyrrolopyridyl, furopyridyl, indolyl, benzofuryl, benzothiofuryl, benzoindolyl, benzothienyl, pyrazolyl, piperidyl, piperazinyl, indolinyl, morpholinyl, benzoxazolyl, pyrroloquinolyl, pyrrolo[2,3-b]pyridinyl, benzotriazolyl, oxobenzo-oxazolyl, benco[1,3]dioxolyl, benxzoimidazolyl, quinolinyl, indanyl and the like. Heteroaryls are within the scope of the definition of het. Examples of heteroaryls are pyridyl, pyrimidinyl, quinolyl, thiazolyl and benzothiazolyl. The most preferred het are pyridyl, pyrimidinyl and thiazolyl. The het may be unsubstituted or substituted as described herein. It is preferred that it is unsubstituted or if substituted it is substituted on a carbon atom by halogen, especially fluorine or chlorine, hydroxy, $C_1$-$C_4$ alkyl, such as methyl and ethyl, $C_1$-$C_4$ alkoxy, especially methoxy and ethoxy, nitro, —O—C(O)—$C_1$-$C_4$alkyl or —C(O)—O—$C_1$-$C_4$alkyl, SCN or nitro or on a nitrogen atom by $C_1$-$C_4$ alkyl, especially methyl or ethyl, —O—C(O)—$C_1$-$C_4$alkyl or —C(O)—O—$C_1$-$C_4$alkyl, such as carbomethoxy or carboethoxy.

When two substituents together with a commonly bound nitrogen are het, it is understood that the resulting heterocyclic ring is a nitrogen-containing ring, such as aziridine, azetidine, azole, piperidine, piperazine, morphiline, pyrrole, pyrazole, thiazole, oxazole, pyridine, pyrimidine, isoxazole, and the like, wherein such het may be unsubstituted or substituted as defined hereinabove.

"Halo", or halogen is fluorine, chlorine, bromine or iodine, especially fluorine and chlorine.

Unless otherwise specified "alkyl", either above or in combination, includes straight or branched chain alkyl, such as methyl, ethyl, n-propyl, isopropyl, n-butyl, sec-butyl, tert-butyl, n-pentyl and branched pentyl, n-hexyl and branched hexyl, and the like.

Unsubstituted is intended to mean that hydrogen is the only substituent.

Except as described herein, any of the above defined aryl, het, alkyl, alkenyl, alkynyl, or cycloalkyl, may be unsubstituted or independently substituted by up to four, preferably one, two or three substituents, selected from the group consisting of: halo (such as Cl or Br); hydroxy; lower alkyl (such as $C_1$-$C_3$ alkyl); lower alkyl which may be substituted with any of the substituents defined herein; lower alkenyl; lower alkynyl; lower alkanoyl; lower alkoxy (such as methoxy); aryl (such as phenyl or naphthyl); substituted aryl (such as fluoro phenyl or methoxy phenyl); aryl lower alkyl such as benzyl, amino, mono or di-lower alkyl (such as dimethylamino); lower alkanoyl amino acetylamino; amino lower alkoxy (such as ethoxyamine); nitro; cyano; cyano lower alkyl; carboxy; lower carbalkoxy (such as methoxy carbonyl; n-propoxy carbonyl or iso-propoxy carbonyl), lower aryloyl, such as benzoyl; carbamoyl; N-mono- or N,N di-lower alkyl carbamoyl; lower alkyl carbamic acid ester; amidino; guanidine; ureido; mercapto; sulfo; lower alkylthio; sulfoamino; sulfonamide; benzosulfonamide; sulfonate; sulfanyl lower alkyl (such as methyl sulfanyl); sulfoamino; aryl sulfonamide; halogen substituted or unsubstituted aryl sulfonate (such as chloro-phenyl sulfonate); lower alkylsulfinyl; arylsulfinyl; aryl-lower alkylsulfinyl; lower alkylarylsulfinyl; lower alkanesulfonyl; arylsulfonyl; aryl-lower alkylsulfonyl; lower aryl alkyl; lower alkylarylsulfonyl; halogen-lower alkylmercapto; halogen-lower alkylsulfonyl; such as trifluoromethane sulfonyl; phosphono(—P(=O)(OH)$_2$); hydroxy-lower alkoxy phosphoryl or di-lower alkoxyphosphoryl; urea and substituted urea; alkyl carbamic acid ester or carbamates (such as ethyl-N-phenyl-carbamate); or lower alkyl (e.g. methyl, ethyl or propyl).

In an embodiment, the above mentioned alkyl, cycloalkyl, and aryl groups are independently unsubstituted or are substituted by lower alkyl, aryl, aryl lower alkyl, carboxy, lower carbalkoxy and especially halogen, —OH, —SH, —OCH$_3$, —SCH$_3$, —CN, —SCN or nitro.

As used herein, the term "alkylaryl" refers to a aryl group connected to the main chain by a bridging alkylene group. Examples include but are not limited to benzyl, phenethyl, naphthylmethyl, and the like. Similarly, alkyl cyano group refers to a cyano group connected to the main chain by a bridging alkylene group. Also similarly, alkylcycloalkyl, refers to a cycloalkyl group connected to the main chain by a bridging alkylene group. An "alkylhet" group refers to a het group bridged to a main chain through an alkyl group.

The term "arylalkyl" on the other hand, refers to an alkyl group bridged to the main chain through an aryl group, such as a phenylene group. Examples include but are not limited to methylphenyl, ethylphenyl, and the like. Similarly, an "arylcycloalkyl" group refers to a cycloalkyl group bridged to the main chain through an aryl group.

The term "hetcycloalkyl" refers to a cycloalkyl group bridged to the main chain by a het group. A "cycloalkylaryl" group refers to an aryl group bridged to the main chain by a cycloalkyl group, and a "cycloalkylhet" group refers to a het group bridged to the main chain by a cycloalkyl group. Each of "hetcycloalkyl," "cycloalkylaryl," and "cycloalkylhet" may be merged rings of the two groups.

The term "alkoxy" refers to an alkyl group as defined herein, connected to the main chain by an oxygen atom. An "alkoxy" group also refers to an alkyl group with ether functionality included therein; i.e., an alkyl group with an oxygen —O— included in the main chain in any position. Examples include but are not limited to methoxy, ethoxy, and the like.

It is to be understood that the terminology C(O) refers to a —C=O group, whether it be ketone, aldehyde or acid or acid derivative. Similarly, S(O) refers to a —S=O group. A "hydroxyl" group refers to an —OH group.

Use in Cancer, and Autoimmune Diseases

The compounds of the present invention have valuable pharmacological properties and are useful in the treatment of diseases. In certain embodiments, compounds of the invention are useful in the treatment of a proliferative disease, or cancer.

A proliferative disease is mainly a tumor disease (or cancer) (and/or any metastases). The inventive compounds are particularly useful for treating a tumor which is a breast cancer, genitourinary cancer, lung cancer, gastrointestinal cancer, epidermoid cancer, multiple myeloma, melanoma, ovarian cancer, pancreas cancer, neuroblastoma, nose, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multidrug resistance.

In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original organ or tissue and/or in any other location are implied alternatively or in addition, whatever the location of the tumor and/or metastasis.

The inventive compound is selectively toxic or more toxic to rapidly proliferating cells than to normal cells, particularly in human cancer cells, e.g., cancerous tumors, the compound has significant antiproliferative effects and promotes differentiation, e.g., cell cycle arrest and apoptosis.

In still other certain embodiments, compounds of the invention are useful in the treatment of autoimmune diseases. Examples of autoimmune diseases to be treated by the compounds of the invention include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis, multiple sclerosis, neuritis, uveitis ophthalmia, polyendocrinopathies, purpura, Reiter's Disease, Stiff-Man Syndrome, autoimmune pulmonary inflammation, autism, Guillain-Barre Syndrome, insulin dependent diabetes mellitis, autoimmune inflammatory eye, autoimmune thyroiditis, hypothyroidism, systemic lupus erhythematosus, Goodpasture's syndrome, Pemphigus, Receptor autoimmunities, autoimmune hemolytic anemia, autoimmune thrombocytopenic purpura, rheumatoid arthritis, mixed connective tissue disease, polymyositis/dermatomyositis, pernicious anemia, idiopathic Addison's disease, infertility, glomerulonephritis, bullous pemphigoid, Sjogren's syndrome, diabetes millitus, adrenergic drug resistance, chronic active hepatitis, primary biliary cirrhosis, vitiligo, vasculitis, post-MI, cardiotomy syndrome, urticaria, atopic dermatitis, asthma, inflammatory myopathies, chronic active hepatitis, primary biliary cirrhosis and T-cell mediated hypersensitivity diseases.

It is also contemplated that compound of the present invention are useful in treating ophthalmic diseases including age related macular degeneration The term "use" includes any one or more of the following embodiments of the invention, respectively: the use in the treatment of protein kinase-associated disorders; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from cancer, transplant rejections, or autoimmune diseases, as well as those diseases that depend on the activity of protein kinases. The term "use" further includes embodiments of compositions herein which bind to a protein kinase sufficiently to serve as tracers or labels, so that when coupled to a fluor or tag, or made radioactive, can be used as a research reagent or as a diagnostic or an imaging agent.

Assays

The inhibition of protein kinase activity by the compounds of the invention may be measured using a number of assays available in the art. Examples of such assays are described in the Exemplification section below.

Pharmaceutical Compositions

The language "effective amount" of the compound is that amount necessary or sufficient to treat or prevent a protein kinase-associated disorder, e.g. prevent the various morphological and somatic symptoms of a protein kinase-associated disorder, and/or a disease or condition described herein. In an example, an effective amount of the compound of the invention is the amount sufficient to treat a protein kinase-associated disorder in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a protein kinase-associated disorder. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, $\alpha$-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a protein kinase-associated disorder.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Synthetic Procedure

Compounds of the present invention are prepared from commonly available compounds using procedures known to those skilled in the art, including any one or more of the following conditions without limitation: Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Deriva-*

*tives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage). Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials. Intermediates and final products can be worked up and/or purified according to standard methods, e.g., using chromatographic methods, distribution methods, (re-) crystallization, and the like.

General Process Conditions

The following applies in general to all processes mentioned throughout this disclosure.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the $H^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Prodrugs

This invention also encompasses pharmaceutical compositions containing, and methods of treating protein kinase-associated disorders through administering, pharmaceutically acceptable prodrugs of compounds of the compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Any reference to a compound of the present invention is therefore to be understood as referring also to the corresponding pro-drugs of the compound of the present invention, as appropriate and expedient.

Combinations

A compound of the present invention may also be used in combination with other agents, e.g., an additional protein kinase inhibitor that is or is not a compound of the invention, for treatment of a protein kinase-associated disorder in a subject.

By the term "combination" is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

The compounds of the invention may be administered, simultaneously or sequentially, with an antiinflammatory, antiproliferative, chemotherapeutic agent, immunosuppressant, anti-cancer, cytotoxic agent or kinase inhibitor other than a compound of the Formula I or salt thereof. Further examples of agents that may be administered in combination with the compounds of the invention include, but are not limited to, a PTK inhibitor, cyclosporin A, CTLA4-Ig, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal antiinflammatory drugs, steroids, gold compounds, antiproliferative agents, FK506, mycophenolate mofetil, cytotoxic drugs, TNF-α inhibitors, anti-TNF antibodies or soluble TNF receptor, rapamycin, leflunimide, cyclooxygenase-2 inhibitors, paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

Exemplification of the Invention

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

General Synthesis Methods

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

| LIST OF ABBREVIATONS | |
|---|---|
| BINAP | (±)-(1,1'-binaphthalene-2-2'diyl)bis(diphenylphosphine) |
| DIEA | Diethylamine |
| DIPEA | Diisoproylethylamine |
| DMF | Dimethylformamide |
| HPLC | High pressure liquid chromatography |
| HRMS | High resolution mass spectrometry |
| HBTU | O-Benzotriazol-1-yl-N,N,N',N'-tetramethyluronium hexafluorophosphate |
| HOBt | 1-Hydroxy-1H-benzotriazol |
| LC/MS | Liquid chromatography/mass spectrometry |
| NMM | N-methylmorpholine |
| NMP | N-methylpyrrolidine |
| RT | room temperature |
| THF | Tetrahydrofuran |
| Et | Ethyl |
| NBS | N-Bromosuccinimide |
| DIAD | Diisopropyl azo dicarboxylate |
| Ts | Tosyl |
| TBAF | Tetra-n-butylammonium fluoride |

EXAMPLES

The compounds of the present invention can be prepared according to the following methods.

Example 1 and 14

[4-(5-Isopropyl-1H-pyrazol-4-yl)-pyridin-2-yl]-(2-methyl-benzyl)-amine

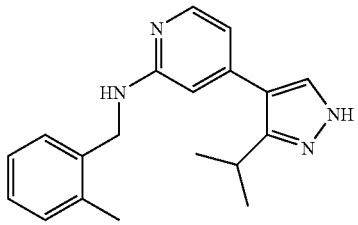 [SMILES: Cc1ccccc1CNc1cc(-c2c[nH]nc2C(C)C)ccn1]

To a solution of diisopropylamine (12.6 mL, 89.9 mmol) in anhydrous THF (50 mL) is added n-butyllithium (42.2 mL of an 1.6M in hexane) dropwise at 0° C. After 30 min at 0° C., 2-fluoro-4-methylpyridine (5 g, 45 mmol) is added. The resulting mixture is stirred at 0° C. for 30 min. After the addition of methyl isobutyrate (5.4 mL, 47.3 mmol) at 0° C., the reaction mixture is stirred overnight. The reaction mixture is quenched with acetic acid at 0° C., diluted with water, and extracted with ethyl ether. The organic layer is dried over sodium sulfate and concentrated in vacuo. The residue is purified by flash chromatography (SiO$_2$, EtOAc/heptane 7:93 to 60:40) to give 4.8 g of 1-(2-fluoro-pyridin-4-yl)-3-methyl-butan-2-one as a light yellowish solid.

LCMS: 182 (M+H)$^+$

To a solution of 1-(2-fluoro-pyridin-4-yl)-3-methyl-butan-2-one (4.8 g, 26.5 mmol) in anhydrous toluene (20 mL) is added N,N-dimethylformamide dimethylacetal (16.0 mL, 120.6 mmol). The reaction is heated at 90° C. for 4 h. The mixture is concentrated in vacuo to give the crude product, 1-dimethylamino-2-(2-fluoro-pyridin-4-yl)-4-methyl-pent-1-en-3-one. The crude product is used as it is.

LCMS: 237 (M+H)$^+$

To a solution of 1-dimethylamino-2-(2-fluoro-pyridin-4-yl)-4-methyl-pent-1-en-3-one (crude, 26.5 mmol) in methanol (50 mL) is added hydrazine (0.84 mL, 26.5 mmol) at 0° C. The reaction mixture is stirred for 4 h, diluted with EtOAc, and washed with water. The organic layer is washed with brine, dried over sodium sulfate, and concentrated in vacuo.

Purification by flash chromatography (SiO$_2$, EtOAc/heptan 5:1) afforded 3.8 g of 2-fluoro-4-(5-isopropyl-1H-pyrazol-4-yl)-pyridine as a white solid.

LCMS: 206 (M+H)$^+$
$^1$HNMR: (CDCl3, 400 MHz) δ 8.18 (d, 1H), 7.69 (s, 1H), 7.18 (m, 1H), 3.29 (m, 1H), 1.33 (d, 6H).

To a solution of 2-fluoro-4-(5-isopropyl-1H-pyrazol-4-yl)-pyridine (30 mg, 0.15 mmol) in anhydrous DMSO (0.25 mL) is added 2-methyl-benzylamine (37 uL, 0.3 mmol). The reaction mixture is stirred at 150° C. overnight, diluted with EtOAc, and washed with water and brine. The organic layer is dried over sodium sulfate and concentrated in vacuo. The crude product is purified by preparative HPLC to provide 18.8 mg of [4-(5-isopropyl-1H-pyrazol-4-yl)-pyridin-2-yl]-(2-methyl-benzyl)-amine. (Example 1)

LCMS: 307 (M+H)$^+$

Examples 2-82

By repeating the procedures described in example 1, using appropriate starting materials, the following compounds are obtained.

Compounds

TABLE 1

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| 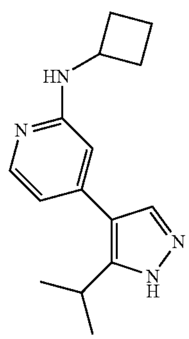 [SMILES: CC(C)c1[nH]ncc1-c1ccnc(NC2CCC2)c1] | 2 | <.5 | <.5 | <.5 | <1 |
| 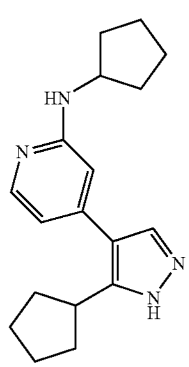 [SMILES: c1cc(-c2cn[nH]c2C2CCCC2)cc(NC2CCCC2)n1] | 3 | <.5 | <.5 | | <1 |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| (structure) | 4 | <1 | <5 | <5 | |
| (structure) | 5 | <5 | <10 | <10 | |
| (structure) | 6 | <5 | <5 | <5 | |
| (structure) | 7 | <.5 | <.5 | <1 | |
| (structure) | 8 | <.5 | <5 | <5 | |

TABLE 1-continued
All values listed are IC50 numbers in umol-1.
| Structure | Example No. | CDK4 HTRF | CDK2 cyA IMAP | hCDK1/B IC50 | CDK4 ELISA assay IC50 |
|---|---|---|---|---|---|
| 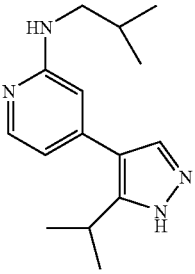 [SMILES: CC(C)CNc1cc(-c2cn[nH]c2C(C)C)ccn1] | 9 | <.5 | <.5 | <.5 | |
| 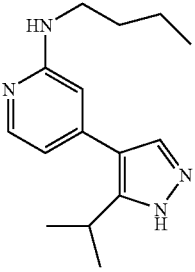 [SMILES: CCCCNc1cc(-c2cn[nH]c2C(C)C)ccn1] | 10 | <.5 | <5 | <5 | |
| 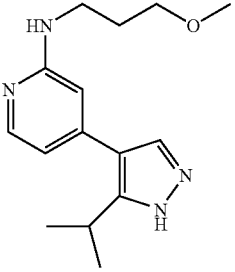 [SMILES: COCCCNc1cc(-c2cn[nH]c2C(C)C)ccn1] | 11 | <1 | <5 | <5 | |
| 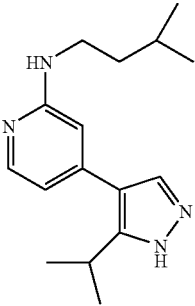 [SMILES: CC(C)CCNc1cc(-c2cn[nH]c2C(C)C)ccn1] | 12 | <1 | <5 | <5 | |
| 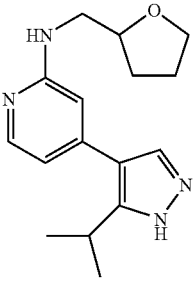 | 13 | <5 | <10 | <5 | |

TABLE 1-continued
| | | All values listed are IC50 numbers in umol-1. | | | |
|---|---|---|---|---|---|
| Structure | Example No. | CDK4 HTRF | CDK2 cyA IMAP | hCDK1/B IC50 | CDK4 ELISA assay IC50 |
| 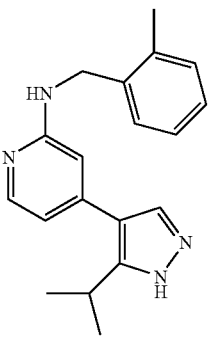 [SMILES: Cc1ccccc1CNc1cc(-c2cn[nH]c2C(C)C)ccn1] | 14 | <.1 | <5 | <5 | |
| 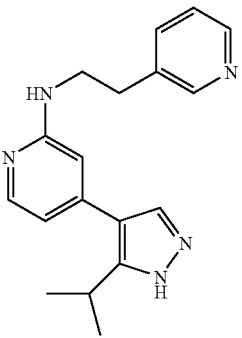 [SMILES: CC(C)c1[nH]ncc1-c1ccnc(NCCc2cccnc2)c1] | 15 | <.5 | <5 | <5 | |
| 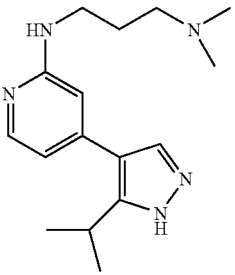 [SMILES: CC(C)c1[nH]ncc1-c1ccnc(NCCCN(C)C)c1] | 16 | <5 | 15 | 15 | <15 |
| 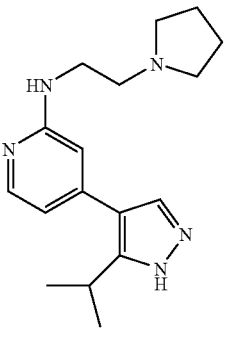 [SMILES: CC(C)c1[nH]ncc1-c1ccnc(NCCN2CCCC2)c1] | 17 | <5 | 15 | 15 | <15 |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| (structure) | 18 | <5 | 15 | 15 | |
| (structure) | 19 | <10 | 15 | 15 | |
| (structure) | 20 | <5 | <5 | <5 | |
| (structure) | 21 | <5 | <10 | <10 | <15 |
| (structure) | 22 | <5 | <5 | <5 | <.5 |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| 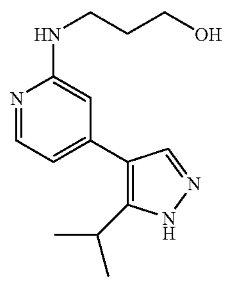 [SMILES: CC(C)c1[nH]ncc1-c1ccnc(NCCCO)c1] | 23 | <5 | <5 | <5 | |
| 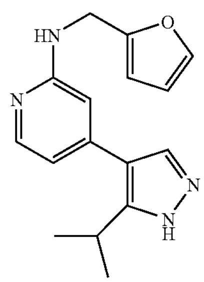 [SMILES: CC(C)c1[nH]ncc1-c1ccnc(NCc2ccco2)c1] | 24 | <1 | <5 | <5 | |
| 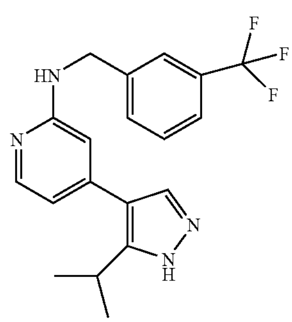 [SMILES: CC(C)c1[nH]ncc1-c1ccnc(NCc2cccc(C(F)(F)F)c2)c1] | 25 | <5 | <5 | <5 | <.1 |
| 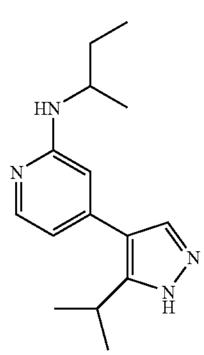 [SMILES: CCC(C)Nc1cc(-c2cn[nH]c2C(C)C)ccn1] | 26 | <.5 | <1 | <5 | |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| 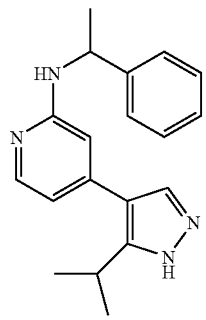 [SMILES: CC(C)c1[nH]ncc1-c1ccnc(NC(C)c2ccccc2)c1] | 27 | <1 | <5 | <5 | |
| 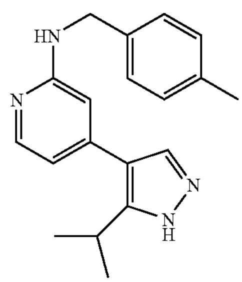 [SMILES: Cc1ccc(CNc2cc(-c3cn[nH]c3C(C)C)ccn2)cc1] | 28 | <5 | <5 | <5 | |
| 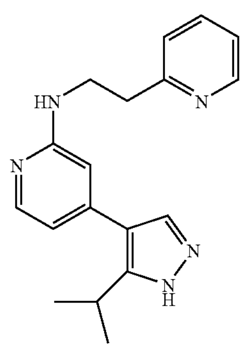 [SMILES: CC(C)c1[nH]ncc1-c1ccnc(NCCc2ccccn2)c1] | 29 | <1 | <5 | <10 | |
| 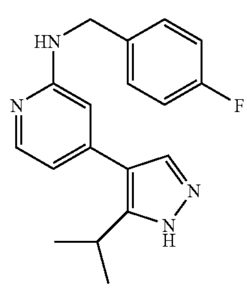 [SMILES: CC(C)c1[nH]ncc1-c1ccnc(NCc2ccc(F)cc2)c1] | 30 | <5 | <5 | <5 | |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| (structure: 2-((2-piperidin-1-ylethyl)amino)pyridine with 4-(5-isopropyl-1H-pyrazol-4-yl) substituent) | 31 | <5 | 15 | 15 | <15 |
| (structure: 2-((2-morpholin-4-ylethyl)amino)pyridine with 4-(5-isopropyl-1H-pyrazol-4-yl) substituent) | 32 | <5 | <10 | 15 | <15 |
| (structure: 2-((4-pyrrolidin-1-ylbutyl)amino)pyridine with 4-(5-isopropyl-1H-pyrazol-4-yl) substituent) | 33 | <5 | 15 | 15 | |
| (structure: 2-((4-methoxybenzyl)amino)pyridine with 4-(5-isopropyl-1H-pyrazol-4-yl) substituent) | 34 | <5 | <5 | <5 | |

TABLE 1-continued

| All values listed are IC50 numbers in umol-1. | | | | | |
|---|---|---|---|---|---|
| Structure | Example No. | CDK4 HTRF | CDK2 cyA IMAP | hCDK1/B IC50 | CDK4 ELISA assay IC50 |
| | 35 | <5 | <5 | <5 | <15 |
| | 36 | <10 | 15 | 15 | <15 |
| | 37 | <.5 | <1 | <5 | |
| | 38 | <1 | <5 | <5 | |

TABLE 1-continued

| Structure | Example No. | CDK4 HTRF | CDK2 cyA IMAP | hCDK1/B IC50 | CDK4 ELISA assay IC50 |
|---|---|---|---|---|---|
| 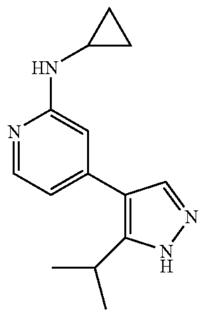 [SMILES: CC(C)c1[nH]ncc1-c1ccnc(NC2CC2)c1] | 39 | <.5 | <1 | <5 | |
| 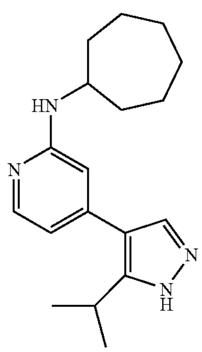 [SMILES: CC(C)c1[nH]ncc1-c1ccnc(NC2CCCCCC2)c1] | 40 | <.5 | <.5 | <1 | |
| 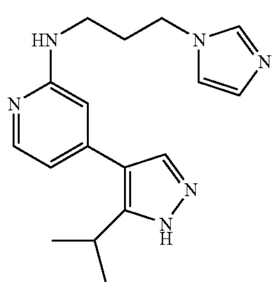 [SMILES: CC(C)c1[nH]ncc1-c1ccnc(NCCCn2ccnc2)c1] | 41 | <5 | <1 | <.5 | |
| 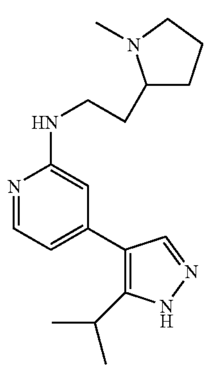 [SMILES: CC(C)c1[nH]ncc1-c1ccnc(NCCC2CCCN2C)c1] | 42 | <5 | 15 | 15 | <15 |

All values listed are IC50 numbers in umol-1.

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| (indanyl-NH-pyridine-pyrazole-isopropyl) | 43 | <.5 | <5 | <5 | |
| (propyl-NH-pyridine-pyrazole-isopropyl) | 44 | <.5 | <5 | <5 | |
| (N-benzylpiperidinyl-NH-pyridine-pyrazole-isopropyl) | 45 | <.5 | 15 | <15 | |
| (isobutyl-hydroxymethyl-NH-pyridine-pyrazole-isopropyl) | 46 | <.5 | <15 | <10 | |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| (4-piperidinylmethylamino-pyridinyl isopropyl pyrazole) | 47 | <10 | 15 | 15 | <15 |
| (phenylamino-pyridinyl isopropyl pyrazole) | 48 | <.1 | <.05 | <.1 | <1 |
| (3-methylbenzylamino-pyridinyl isopropyl pyrazole) | 49 | <5 | <5 | <5 | |
| (2-trifluoromethylbenzylamino-pyridinyl isopropyl pyrazole) | 50 | <1 | <5 | <5 | |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| 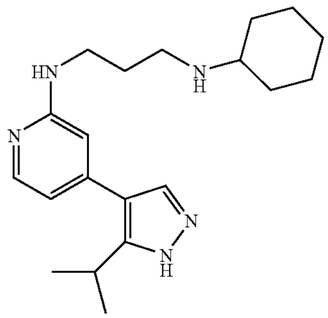 [SMILES: CC(C)c1[nH]ncc1-c1ccnc(NCCCNC2CCCCC2)c1] | 51 | <5 | 15 | 15 | <15 |
| 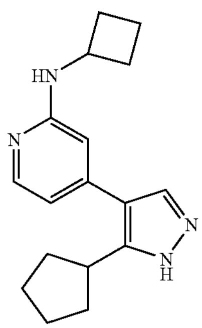 [SMILES: c1cc(-c2cn[nH]c2C2CCCC2)cc(NC2CCC2)n1] | 52 | <.5 | <.5 | | <5 |
| 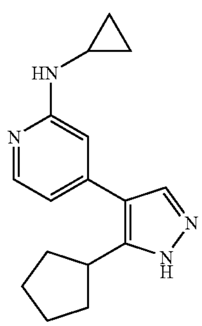 [SMILES: c1cc(-c2cn[nH]c2C2CCCC2)cc(NC2CC2)n1] | 53 | <.5 | <1 | | <5 |
| 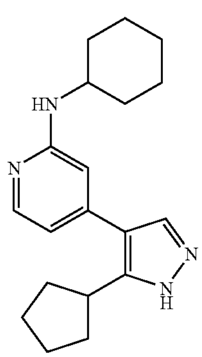 [SMILES: c1cc(-c2cn[nH]c2C2CCCC2)cc(NC2CCCCC2)n1] | 54 | <.5 | <1 | | <5 |

TABLE 1-continued
All values listed are IC50 numbers in umol-1.
| Structure | Example No. | CDK4 HTRF | CDK2 cyA IMAP | hCDK1/B IC50 | CDK4 ELISA assay IC50 |
|---|---|---|---|---|---|
| 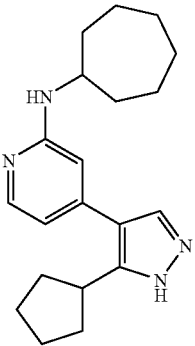 [SMILES: c1cc(-c2cn[nH]c2C2CCCC2)cc(NC2CCCCCC2)n1] | 55 | <.5 | <1 | <5 | |
| 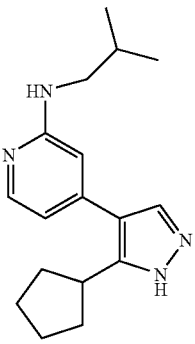 [SMILES: CC(C)CNc1cc(-c2cn[nH]c2C2CCCC2)ccn1] | 56 | <.5 | <1 | <5 | |
| 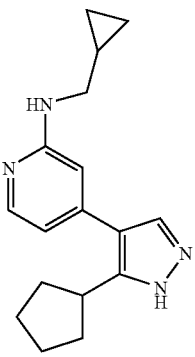 [SMILES: c1cc(-c2cn[nH]c2C2CCCC2)cc(NCC2CC2)n1] | 57 | <1 | <5 | <5 | |
| 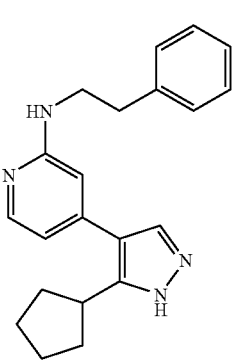 [SMILES: c1ccc(CCNc2cc(-c3cn[nH]c3C3CCCC3)ccn2)cc1] | 58 | <.5 | <5 | <5 | |

TABLE 1-continued
| All values listed are IC50 numbers in umol-1. | | | | | |
|---|---|---|---|---|---|
| Structure | Example No. | CDK4 HTRF | CDK2 cyA IMAP | hCDK1/B IC50 | CDK4 ELISA assay IC50 |
| 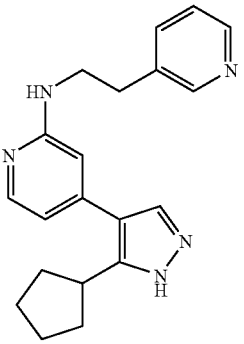 [SMILES: c1cncc(CCNc2cc(-c3cn[nH]c3C3CCCC3)ccn2)c1] | 59 | <.5 | <5 | <5 | |
| 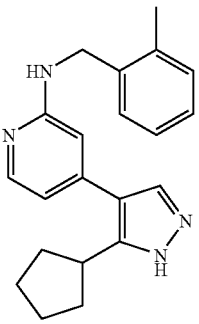 [SMILES: Cc1ccccc1CNc1cc(-c2cn[nH]c2C2CCCC2)ccn1] | 60 | <.5 | <5 | <5 | |
| 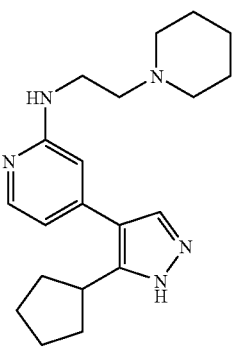 [SMILES: c1cc(-c2cn[nH]c2C2CCCC2)cc(NCCN2CCCCC2)n1] | 61 | <5 | 15 | 15 | <15 |
| 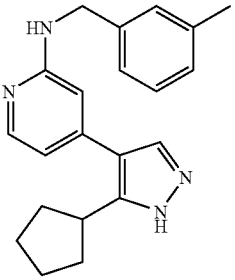 [SMILES: Cc1cccc(CNc2cc(-c3cn[nH]c3C3CCCC3)ccn2)c1] | 62 | <5 | <5 | <5 | |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| 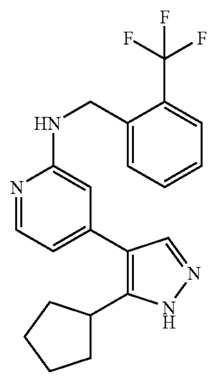 [SMILES: FC(F)(F)c1ccccc1CNc1cc(-c2cn[nH]c2C2CCCC2)ccn1] | 63 | <10 | <5 | <5 | |
| 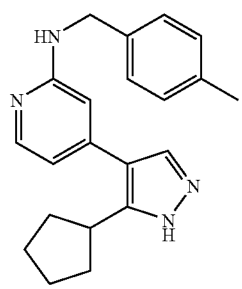 [SMILES: Cc1ccc(CNc2cc(-c3cn[nH]c3C3CCCC3)ccn2)cc1] | 64 | <10 | <5 | <5 | <5 |
| 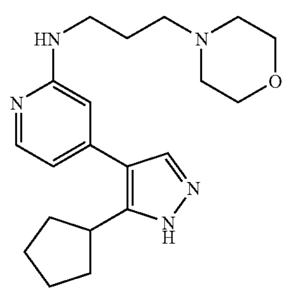 [SMILES: c1cc(-c2cn[nH]c2C2CCCC2)cc(NCCCN2CCOCC2)n1] | 65 | <5 | 15 | 15 | <15 |
| 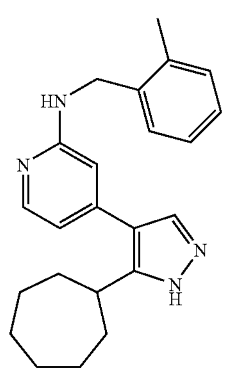 [SMILES: Cc1ccccc1CNc1cc(-c2cn[nH]c2C2CCCCCC2)ccn1] | 66 | <5 | <10 | <10 | <15 |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| 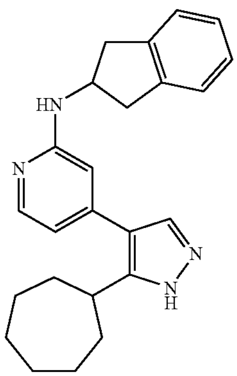 [SMILES: c1ccc2c(c1)CC(Nc1cc(-c3cn[nH]c3C3CCCCCC3)ccn1)C2] | 67 | <5 | <1 | <5 | |
| 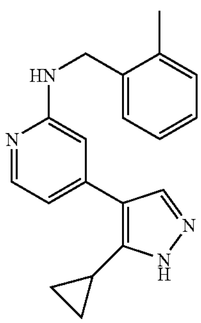 [SMILES: Cc1ccccc1CNc1cc(-c2cn[nH]c2C2CC2)ccn1] | 68 | <.1 | <5 | <5 | |
| 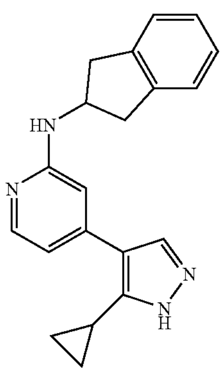 [SMILES: c1ccc2c(c1)CC(Nc1cc(-c3cn[nH]c3C3CC3)ccn1)C2] | 69 | <.1 | <1 | <1 | |
| 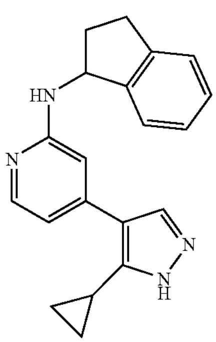 [SMILES: c1ccc2c(c1)CCC2Nc1cc(-c2cn[nH]c2C2CC2)ccn1] | 70 | <.5 | <5 | <5 | |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| (structure) | 71 | <.5 | <5 | <5 | |
| (structure) | 72 | <1 | <5 | <1 | |
| (structure) | 73 | <1 | <10 | <5 | |
| (structure) | 74 | <5 | <5 | <5 | |

TABLE 1-continued

All values listed are IC50 numbers in umol-1.

| Structure | Example No. | CDK4 HTRF | CDK2 cyA IMAP | hCDK1/B IC50 | CDK4 ELISA assay IC50 |
|---|---|---|---|---|---|
| 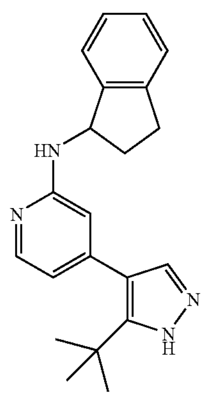 [SMILES: CC(C)(C)c1[nH]ncc1-c1ccnc(NC2CCc3ccccc32)c1] | 75 | <15 | 15 | 15 | |
| 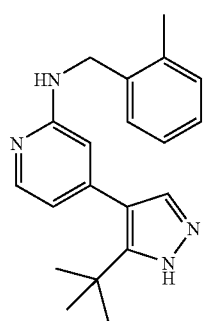 [SMILES: Cc1ccccc1CNc1cc(-c2cn[nH]c2C(C)(C)C)ccn1] | 76 | <10 | 15 | <15 | |
| 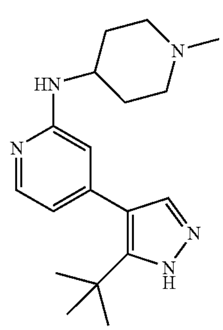 [SMILES: CN1CCC(Nc2cc(-c3cn[nH]c3C(C)(C)C)ccn2)CC1] | 77 | <15 | <15 | 15 | |
| 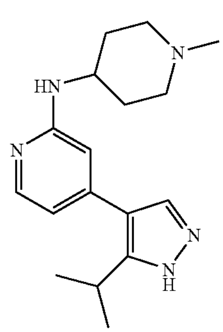 [SMILES: CC(C)c1[nH]ncc1-c1ccnc(NC2CCN(C)CC2)c1] | 78 | <.5 | <15 | <10 | |

TABLE 1-continued
All values listed are IC50 numbers in umol-1.
| Structure | Example No. | CDK4 HTRF | CDK2 cyA IMAP | hCDK1/B IC50 | CDK4 ELISA assay IC50 |
|---|---|---|---|---|---|
| 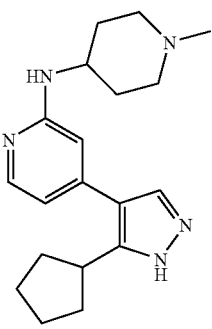 [SMILES: CN1CCC(Nc2cc(-c3cn[nH]c3C3CCCC3)ccn2)CC1] | 79 | <5 | 15 | <10 | |
| 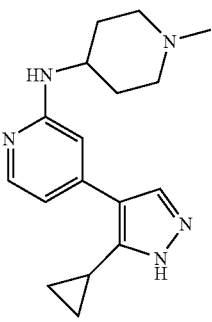 [SMILES: CN1CCC(Nc2cc(-c3cn[nH]c3C3CC3)ccn2)CC1] | 80 | <.5 | 15 | <15 | |
| 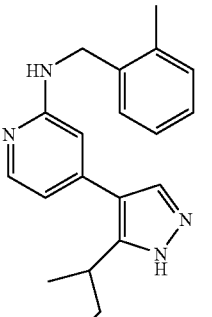 | 81 | <1 | <5 | <5 | |
| 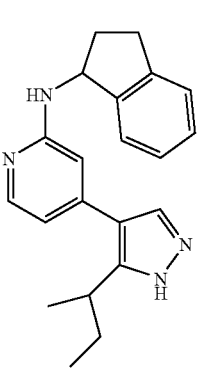 [SMILES: CCC(C)c1[nH]ncc1-c1ccnc(NC2CCc3ccccc32)c1] | 82 | <5 | <5 | <5 | |

Example 83 and 176

(R)-Indan-1-yl-[4-(3-isopropyl-1H-pyrazol-4-yl)-pyrimidin-2-yl]-amine

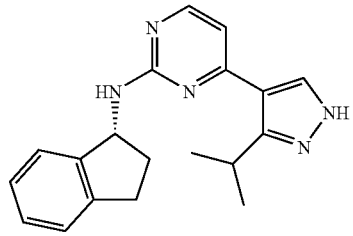 [SMILES: CC(C)c1n[nH]cc1-c1ccnc(N[C@@H]2CCc3ccccc32)n1]

To a solution of diisopropylamine (10.1 mL, 71.8 mmol) in anhydrous THF (50 mL) is added n-butyllithium (33.6 mL of an 1.6M in hexane) dropwise at 0° C. After 30 min at 0° C., 4-methyl-2-(methylthio)pyrimidine (5 mL, 35.9 mmol) is added. The resulting mixture is stirred at 0° C. for 30 min. After the addition of methyl isobutyrate (4.3 mL, 37.7 mmol) at 0° C., the reaction mixture is stirred overnight. The reaction mixture is quenched with acetic acid at 0° C., diluted with water, and extracted with ethyl ether. The organic layer is dried over sodium sulfate and concentrated in vacuo. The residue is purified by flash chromatography (SiO$_2$, EtOAc/heptane 7:93 to 40:60) to give 4.3 g of 3-methyl-1-(2-methylsulfanyl-pyrimidin-4-yl)-butan-2-one.

LCMS: 211.1 (M+H)$^+$

To a solution of 3-methyl-1-(2-methylsulfanyl-pyrimidin-4-yl)-butan-2-one (4.3 g, 20.5 mmol) in anhydrous toluene (20 mL) is added N,N-dimethylformamide dimethylacetal (15.0 mL, 112.9 mmol). The reaction is heated at 90° C. for 4 h. The mixture is concentrated in vacuo to give the crude product, 1-dimethylamino-4-methyl-2-(2-methylsulfanyl-pyrimidin-4-yl)-pent-1-en-3-one. The crude product is used as it is.

LCMS: 266.3 (M+H)$^+$

To a solution of 1-dimethylamino-4-methyl-2-(2-methyl-sulfanyl-pyrimidin-4-yl)-pent-1-en-3-one (crude, 20.5 mmol) in methanol (20 mL) is added hydrazine (0.65 mL, 20.5 mmol) at 0° C. The reaction mixture is stirred for 4 h, diluted with EtOAc, and washed with water. The organic layer is washed with brine, dried over sodium sulfate, and concentrated in vacuo. Purification by flash chromatography (SiO$_2$, EtOAc/heptan 5:1) afforded 4.28 g of 4-(3-isopropyl-1H-pyrazol-4-yl)-2-methylfulfanyl-pyrimidine as a yellow solid.

LCMS: 235.1 (M+H)$^+$

To a solution of 4-(3-isopropyl-1H-pyrazol-4-yl)-2-methylfulfanyl-pyrimidine (2.0 g, 8.5 mmol) in dichloromethane (25 mL) is added mCPBA (5.2 g, 21.3 mmol) at 0° C. The reaction mixture is stirred for 2 h, quenched with 20% Na$_2$S$_2$O$_3$ aqueous solution, and extracted with dichloromethane. The extract is washed with saturated NaHCO$_3$ solution and brine, dried over sodium sulfate, and concentrated in vacuo. The residue is purified by flash chromatography (SiO$_2$, EtOAc/heptane 10:1) to give 1.79 g of 4-(3-isopropyl-1H-pyrazol-4-yl)-2-methanesulfonyl-pyrimidine as a white solid.

LCMS: 267.1 (M+H)$^+$

To a solution of 4-(3-isopropyl-1H-pyrazol-4-yl)-2-methanesulfonyl-pyrimidine (40 mg, 0.15 mmol) in anhydrous DMSO (0.25 mL) is added (R)-indan-1-ylamine (58 uL, 0.45 mmol). The reaction mixture is stirred at 150° C. overnight, diluted with dichloromethane, and washed with water. The organic layer is dried over sodium sulfate and concentrated in vacuo. The crude product is purified by preparative HPLC to provide 20 mg of (R)-indan-1-yl-[4-(3-isopropyl-1H-pyrazol-4-yl)-pyrimidin-2-yl]-amine. (Example 83).

LCMS: 320.2 (M+H)$^+$

Examples 84-191

By repeating the procedures described in example 83, using appropriate starting materials, the following compounds are obtained.

TABLE 2

| | | CDK4 HTRF/ | hCDK1/B/ | CDK2cyA IMAP/ | p_pRb Cap EL/ |
|---|---|---|---|---|---|
| Structure | Example Number | IC50 [umol I-1] | IC50 [umol I-1] | IC50 [umol I-1] | IC50_ppRbin h [umol I-1] |
| | 84 | <1 | <5 | <5 | |
| | 85 | <.05 | <.5 | <1 | <10 |

All values listed are IC50 numbers in umol-1.

TABLE 2-continued
All values listed are IC50 numbers in umol-1.
| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbin h [umol l-1] |
|---|---|---|---|---|---|
| 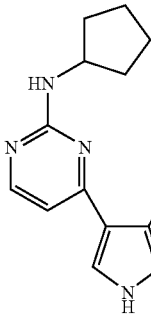 | 86 | <1 | <5 | <5 | |
| 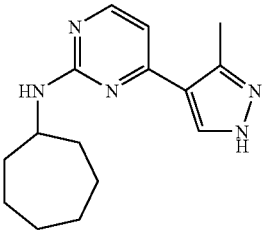 [SMILES: Cc1n[nH]cc1-c1ccnc(NC2CCCCCC2)n1] | 87 | <1 | <5 | <5 | |
| 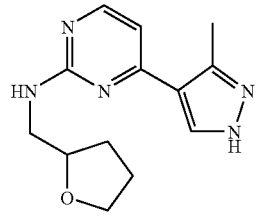 [SMILES: Cc1n[nH]cc1-c1ccnc(NCC2CCCO2)n1] | 88 | <15 | <15 | 15 | <15 |
| 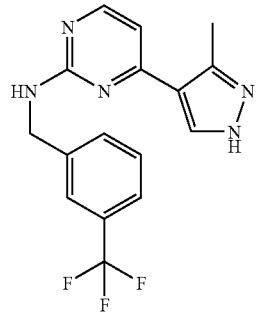 [SMILES: Cc1n[nH]cc1-c1ccnc(NCc2cccc(C(F)(F)F)c2)n1] | 89 | <5 | <10 | <10 | <15 |
| 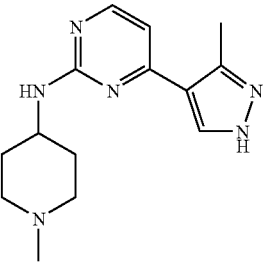 [SMILES: Cc1n[nH]cc1-c1ccnc(NC2CCN(C)CC2)n1] | 90 | <.5 | <15 | <15 | |

TABLE 2-continued
All values listed are IC50 numbers in umol-1.
| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbinh [umol l-1] |
|---|---|---|---|---|---|
| 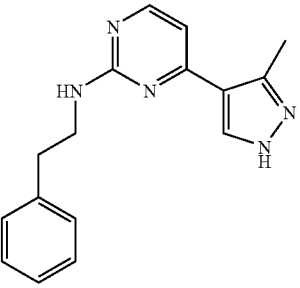 [SMILES: Cc1n[nH]cc1-c1ccnc(NCCc2ccccc2)n1] | 91 | <1 | <10 | <10 | <15 |
| 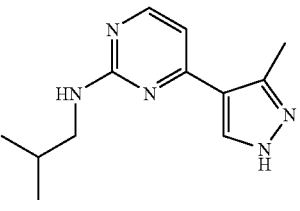 [SMILES: Cc1n[nH]cc1-c1ccnc(NCC(C)C)n1] | 92 | <5 | <5 | <5 | |
| 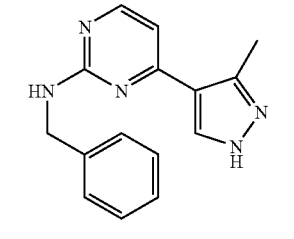 [SMILES: Cc1n[nH]cc1-c1ccnc(NCc2ccccc2)n1] | 93 | <5 | <10 | <15 | <15 |
| 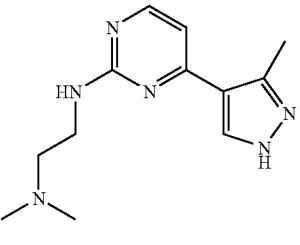 [SMILES: Cc1n[nH]cc1-c1ccnc(NCCN(C)C)n1] | 94 | <10 | 15 | 15 | <15 |
| 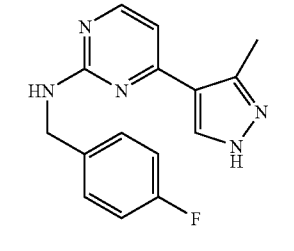 [SMILES: Cc1n[nH]cc1-c1ccnc(NCc2ccc(F)cc2)n1] | 95 | <5 | <10 | <10 | <15 |
| 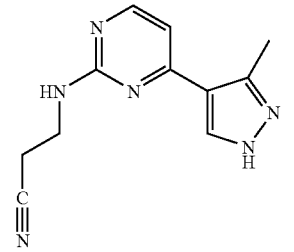 [SMILES: Cc1n[nH]cc1-c1ccnc(NCCC#N)n1] | 96 | <5 | <15 | <15 | <15 |

TABLE 2-continued
All values listed are IC50 numbers in umol-1.
| Structure | Example Number | CDK4 HTRF/ IC50 [umol I-1] | hCDK1/B/ IC50 [umol I-1] | CDK2cyA IMAP/ IC50 [umol I-1] | p_pRb Cap EL/ IC50_ppRbin h [umol I-1] |
|---|---|---|---|---|---|
| 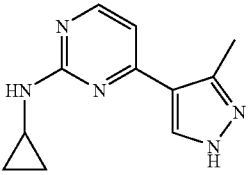 [SMILES: Cc1n[nH]cc1-c1ccnc(NC2CC2)n1] | 97 | <5 | <10 | <10 | <15 |
| 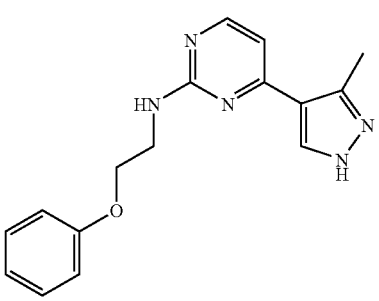 [SMILES: Cc1n[nH]cc1-c1ccnc(NCCOc2ccccc2)n1] | 98 | <5 | <15 | <15 | <15 |
| 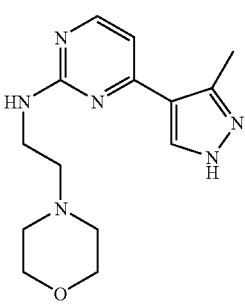 [SMILES: Cc1n[nH]cc1-c1ccnc(NCCN2CCOCC2)n1] | 99 | <10 | 15 | 15 | <15 |
| 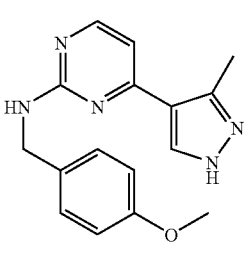 [SMILES: COc1ccc(CNc2nccc(-c3c[nH]nc3C)n2)cc1] | 100 | <5 | <15 | <15 | <15 |
| 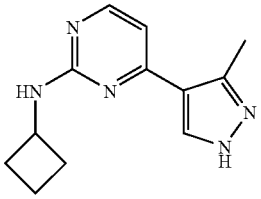 [SMILES: Cc1n[nH]cc1-c1ccnc(NC2CCC2)n1] | 101 | <1 | <5 | <5 | <15 |

TABLE 2-continued
All values listed are IC50 numbers in umol-1.
| Structure | Example Number | CDK4 HTRF/ IC50 [umol I-1] | hCDK1/B/ IC50 [umol I-1] | CDK2cyA IMAP/ IC50 [umol I-1] | p_pRb Cap EL/ IC50_ppRbin h [umol I-1] |
|---|---|---|---|---|---|
| 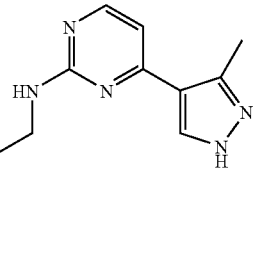 | 102 | <5 | <10 | <10 | <15 |
| 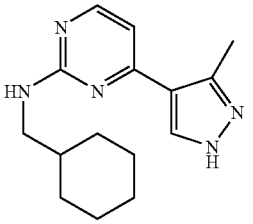 [SMILES: Cc1n[nH]cc1-c1ccnc(NCC2CCCCC2)n1] | 103 | <5 | <10 | <10 | <15 |
| 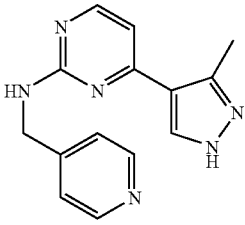 [SMILES: Cc1n[nH]cc1-c1ccnc(NCc2ccncc2)n1] | 104 | <5 | <15 | <15 | <15 |
| 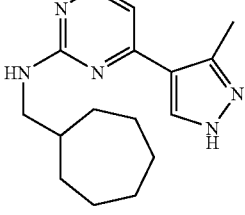 | 105 | <5 | <10 | <15 | <15 |
| 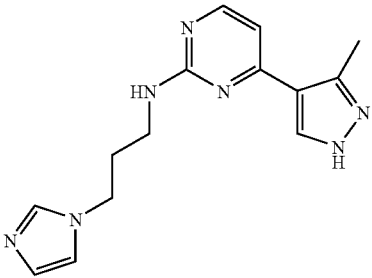 [SMILES: Cc1n[nH]cc1-c1ccnc(NCCCn2ccnc2)n1] | 106 | <5 | <5 | <10 | |

TABLE 2-continued
All values listed are IC50 numbers in umol-1.
| Structure | Example Number | CDK4 HTRF/ IC50 [umol I-1] | hCDK1/B/ IC50 [umol I-1] | CDK2cyA IMAP/ IC50 [umol I-1] | p_pRb Cap EL/ IC50_ppRbin h [umol I-1] |
|---|---|---|---|---|---|
| 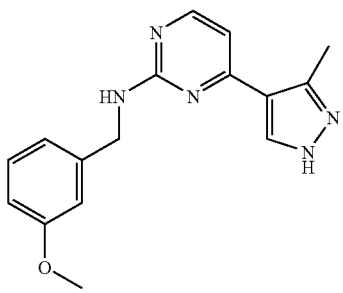 [SMILES: COc1cccc(CNc2nccc(-c3c[nH]nc3C)n2)c1] | 107 | <10 | 15 | 15 | <15 |
| 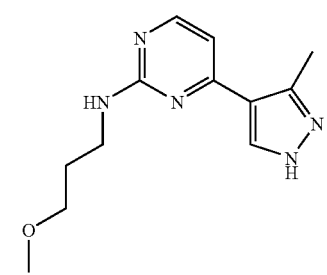 [SMILES: COCCCNc1nccc(-c2c[nH]nc2C)n1] | 108 | <5 | <15 | 15 | <15 |
| 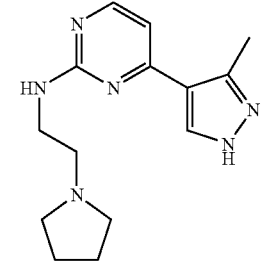 [SMILES: Cc1n[nH]cc1-c1ccnc(NCCN2CCCC2)n1] | 109 | <10 | 15 | 15 | <15 |
| 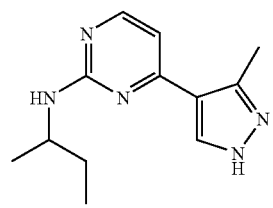 [SMILES: CCC(C)Nc1nccc(-c2c[nH]nc2C)n1] | 110 | <1 | <10 | <5 | <15 |
| 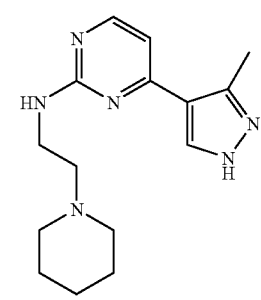 [SMILES: Cc1n[nH]cc1-c1ccnc(NCCN2CCCCC2)n1] | 111 | <10 | 15 | 15 | <15 |

TABLE 2-continued

All values listed are IC50 numbers in umol-1.

| Structure | Example Number | CDK4 HTRF/ IC50 [umol I-1] | hCDK1/B/ IC50 [umol I-1] | CDK2cyA IMAP/ IC50 [umol I-1] | p_pRb Cap EL/ IC50_ppRbin h [umol I-1] |
|---|---|---|---|---|---|
| 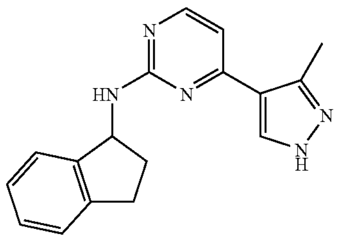 [SMILES: Cc1n[nH]cc1-c1ccnc(NC2CCc3ccccc32)n1] | 112 | <.5 | <10 | <10 | |
| 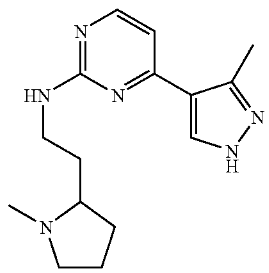 [SMILES: Cc1n[nH]cc1-c1ccnc(NCCC2CCCN2C)n1] | 113 | <10 | 15 | 15 | <15 |
| 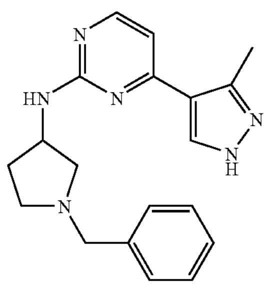 [SMILES: Cc1n[nH]cc1-c1ccnc(NC2CCN(Cc3ccccc3)C2)n1] | 114 | <1 | <10 | <10 | |
| 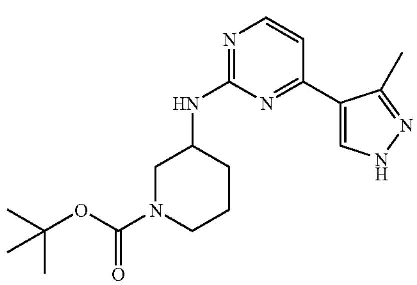 [SMILES: Cc1n[nH]cc1-c1ccnc(NC2CCCN(C(=O)OC(C)(C)C)C2)n1] | 115 | <10 | 15 | 15 | <15 |
| 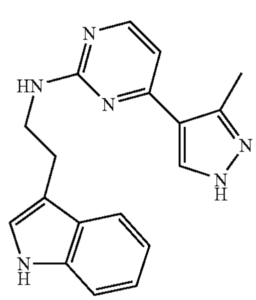 [SMILES: Cc1n[nH]cc1-c1ccnc(NCCc2c[nH]c3ccccc23)n1] | 116 | <5 | <5 | <10 | <15 |

TABLE 2-continued
All values listed are IC50 numbers in umol-1.
| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbin h [umol l-1] |
|---|---|---|---|---|---|
| 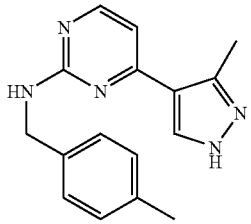 [SMILES: Cc1ccc(CNc2nccc(-c3c[nH]nc3C)n2)cc1] | 117 | <10 | 15 | 15 | <15 |
| 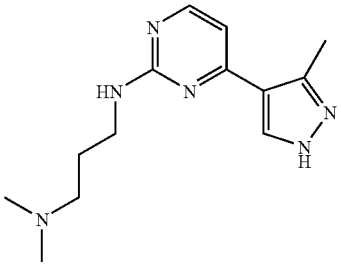 [SMILES: Cc1n[nH]cc1-c1ccnc(NCCCN(C)C)n1] | 118 | <15 | 15 | 15 | <15 |
| 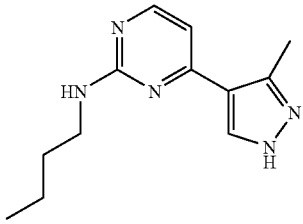 [SMILES: CCCCNc1nccc(-c2c[nH]nc2C)n1] | 119 | <5 | <10 | <10 | <15 |
| 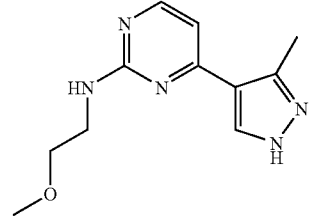 | 120 | <15 | 15 | 15 | <15 |
| 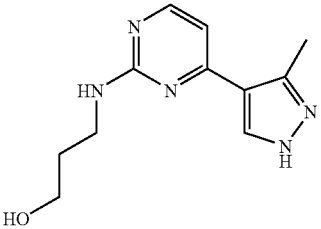 [SMILES: Cc1n[nH]cc1-c1ccnc(NCCCO)n1] | 121 | <5 | <15 | <15 | <15 |
| 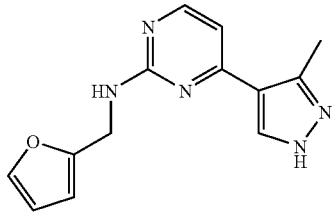 [SMILES: Cc1n[nH]cc1-c1ccnc(NCc2ccco2)n1] | 122 | <10 | 15 | 15 | <15 |

TABLE 2-continued

All values listed are IC50 numbers in umol-1.

| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbin h [umol l-1] |
|---|---|---|---|---|---|
| 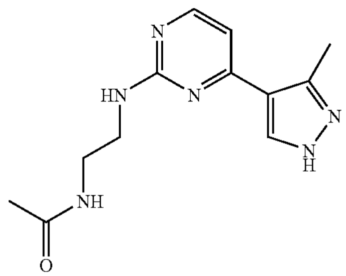 [SMILES: CC(=O)NCCNc1nccc(-c2c[nH]nc2C)n1] | 123 | <5 | <15 | <15 | <15 |
| 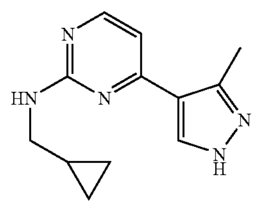 [SMILES: Cc1n[nH]cc1-c1ccnc(NCC2CC2)n1] | 124 | <5 | <10 | <10 | <15 |
| 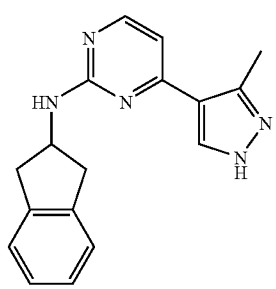 [SMILES: Cc1n[nH]cc1-c1ccnc(NC2Cc3ccccc3C2)n1] | 125 | <.5 | <5 | <5 | |
| 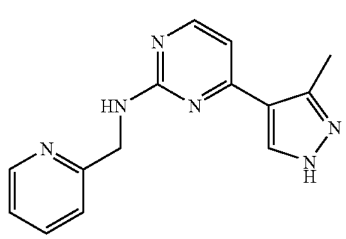 [SMILES: Cc1n[nH]cc1-c1ccnc(NCc2ccccn2)n1] | 126 | <15 | 15 | 15 | <15 |
| 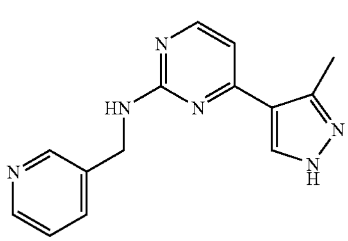 [SMILES: Cc1n[nH]cc1-c1ccnc(NCc2cccnc2)n1] | 127 | <10 | <15 | <10 | <15 |

TABLE 2-continued

All values listed are IC50 numbers in umol-1.

| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbin h [umol l-1] |
|---|---|---|---|---|---|
| 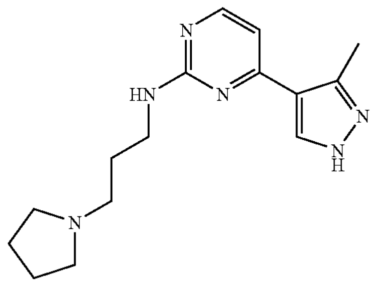 [SMILES: Cc1n[nH]cc1-c1ccnc(NCCCN2CCCC2)n1] | 128 | <15 | 15 | 15 | <15 |
| 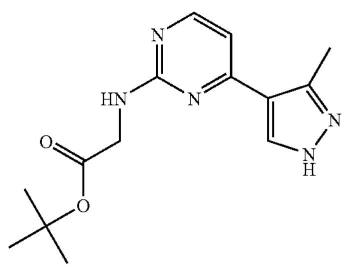 [SMILES: Cc1n[nH]cc1-c1ccnc(NCC(=O)OC(C)(C)C)n1] | 129 | <15 | 15 | 15 | <15 |
| 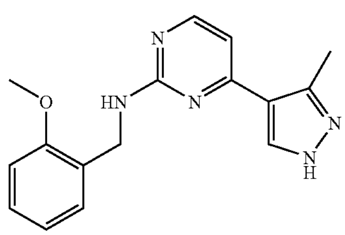 [SMILES: COc1ccccc1CNc1nccc(-c2c[nH]nc2C)n1] | 130 | <5 | <10 | <15 | <15 |
| 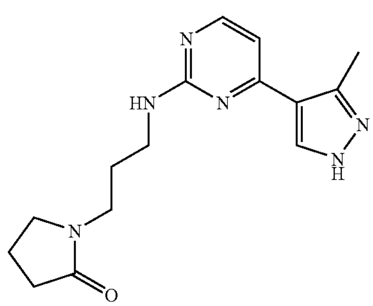 [SMILES: Cc1n[nH]cc1-c1ccnc(NCCCN2CCCC2=O)n1] | 131 | <15 | 15 | 15 | <15 |
| 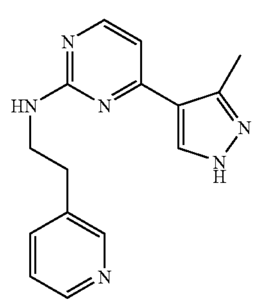 [SMILES: Cc1n[nH]cc1-c1ccnc(NCCc2cccnc2)n1] | 132 | <1 | <10 | <10 | |

TABLE 2-continued
All values listed are IC50 numbers in umol-1.
| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbin h [umol l-1] |
|---|---|---|---|---|---|
| 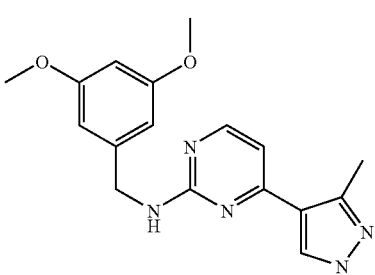 | 133 | <15 | 15 | 15 | <15 |
| 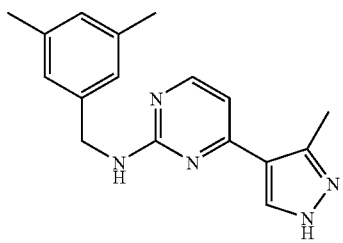 [SMILES: Cc1cc(C)cc(CNc2nccc(-c3c[nH]nc3C)n2)c1] | 134 | <5 | 15 | 15 | <15 |
| 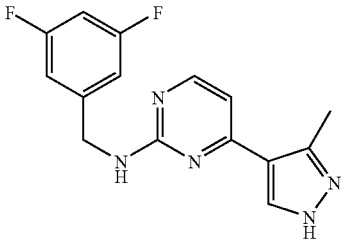 [SMILES: Cc1n[nH]cc1-c1ccnc(NCc2cc(F)cc(F)c2)n1] | 135 | <1 | <5 | <5 | <15 |
| 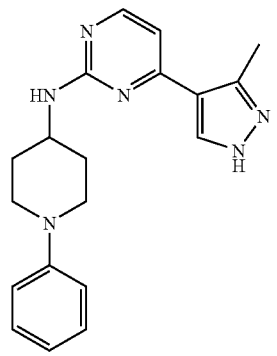 [SMILES: Cc1n[nH]cc1-c1ccnc(NC2CCN(c3ccccc3)CC2)n1] | 136 | <.5 | <5 | <5 | |
| 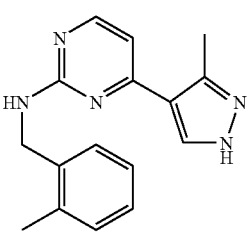 [SMILES: Cc1ccccc1CNc1nccc(-c2c[nH]nc2C)n1] | 137 | <5 | <10 | <10 | |

TABLE 2-continued

All values listed are IC50 numbers in umol-1.

| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbin h [umol l-1] |
|---|---|---|---|---|---|
| 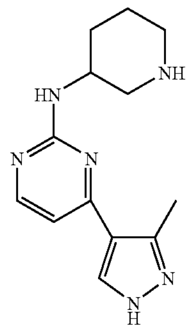 [SMILES: Cc1n[nH]cc1-c1ccnc(NC2CCCNC2)n1] | 138 | <1 | <5 | <5 | |
| 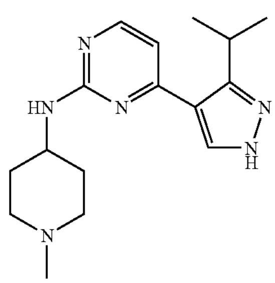 [SMILES: CC(C)c1n[nH]cc1-c1ccnc(NC2CCN(C)CC2)n1] | 139 | <.05 | <.5 | <1 | <5 |
| 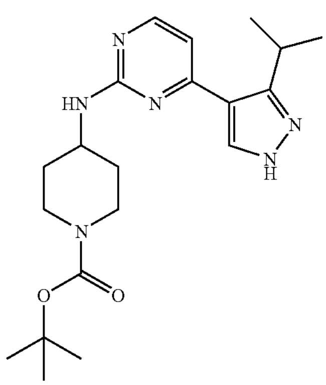 [SMILES: CC(C)c1n[nH]cc1-c1ccnc(NC2CCN(C(=O)OC(C)(C)C)CC2)n1] | 140 | <.05 | <.5 | <1 | |
| 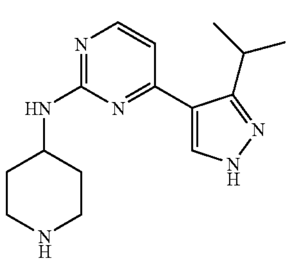 [SMILES: CC(C)c1n[nH]cc1-c1ccnc(NC2CCNCC2)n1] | 141 | <.05 | <.5 | <1 | <5 |

TABLE 2-continued

All values listed are IC50 numbers in umol-1.

| Structure | Example Number | CDK4 HTRF/ IC50 [umol I-1] | hCDK1/B/ IC50 [umol I-1] | CDK2cyA IMAP/ IC50 [umol I-1] | p_pRb Cap EL/ IC50_ppRbin h [umol I-1] |
|---|---|---|---|---|---|
| 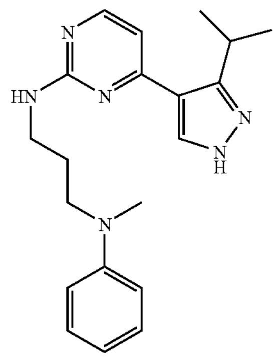 [SMILES: CC(C)c1n[nH]cc1-c1ccnc(NCCCN(C)c2ccccc2)n1] | 142 | <5 | <1 | <5 | |
| 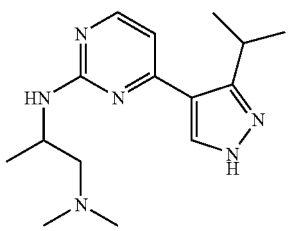 [SMILES: CC(CN(C)C)Nc1nccc(-c2c[nH]nc2C(C)C)n1] | 143 | <.5 | <10 | 15 | |
| 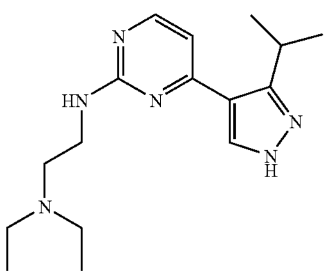 [SMILES: CCN(CC)CCNc1nccc(-c2c[nH]nc2C(C)C)n1] | 144 | <5 | 15 | 15 | <15 |
| 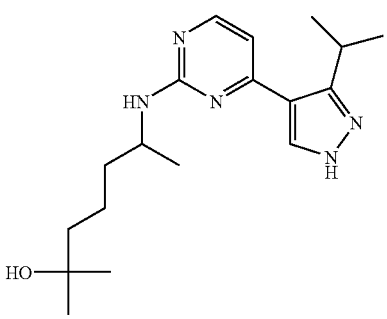 [SMILES: CC(CCCC(C)(C)O)Nc1nccc(-c2c[nH]nc2C(C)C)n1] | 145 | <.5 | <1 | <5 | |
| 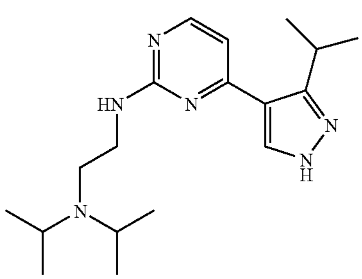 [SMILES: CC(C)c1n[nH]cc1-c1ccnc(NCCN(C(C)C)C(C)C)n1] | 146 | <5 | <5 | 15 | <15 |

TABLE 2-continued
All values listed are IC50 numbers in umol-1.
| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbin h [umol l-1] |
|---|---|---|---|---|---|
| 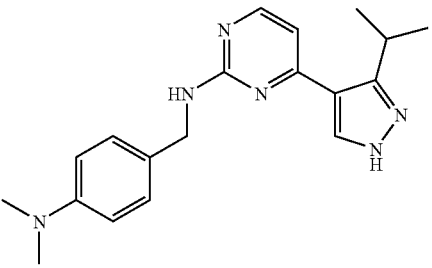 [SMILES: CC(C)c1n[nH]cc1-c1ccnc(NCc2ccc(N(C)C)cc2)n1] | 147 | <5 | <5 | <5 | |
| 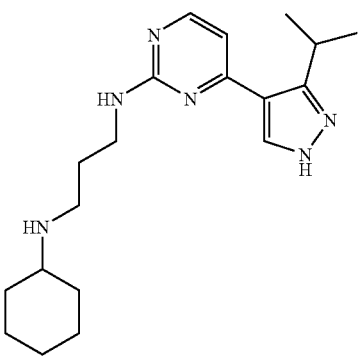 [SMILES: CC(C)c1n[nH]cc1-c1ccnc(NCCCNC2CCCCC2)n1] | 148 | <5 | <15 | <10 | |
| 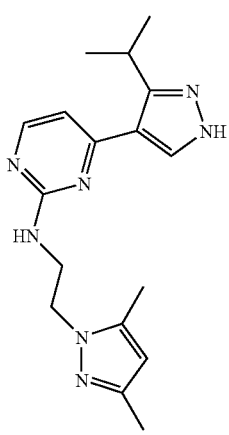 [SMILES: Cc1cc(C)n(CCNc2nccc(-c3c[nH]nc3C(C)C)n2)n1] | 149 | <5 | <10 | <15 | <15 |
| 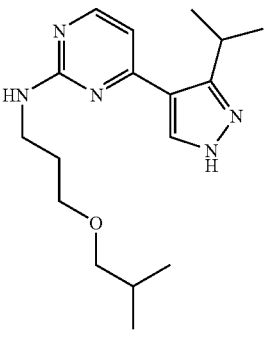 [SMILES: CC(C)COCCCNc1nccc(-c2c[nH]nc2C(C)C)n1] | 150 | <.5 | <1 | <5 | |

TABLE 2-continued

All values listed are IC50 numbers in umol-1.

| Structure | Example Number | CDK4 HTRF/ IC50 [umol I-1] | hCDK1/B/ IC50 [umol I-1] | CDK2cyA IMAP/ IC50 [umol I-1] | p_pRb Cap EL/ IC50_ppRbinh [umol I-1] |
|---|---|---|---|---|---|
| 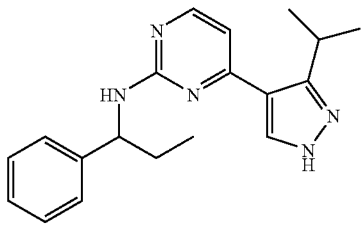 [SMILES: CCC(Nc1nccc(-c2c[nH]nc2C(C)C)n1)c1ccccc1] | 151 | <.5 | <1 | <5 | <10 |
| 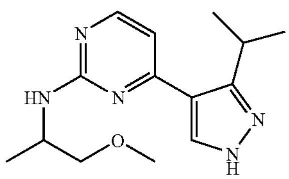 [SMILES: COCC(C)Nc1nccc(-c2c[nH]nc2C(C)C)n1] | 152 | <.5 | <1 | <1 | |
| 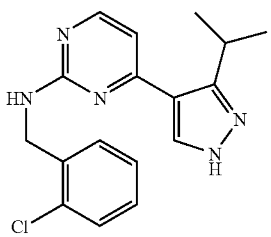 [SMILES: CC(C)c1n[nH]cc1-c1ccnc(NCc2ccccc2Cl)n1] | 153 | <5 | <1 | <1 | |
| 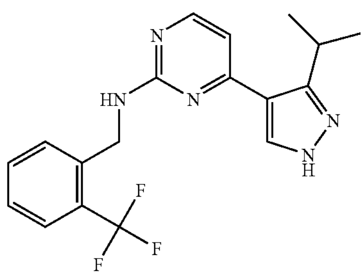 [SMILES: CC(C)c1n[nH]cc1-c1ccnc(NCc2ccccc2C(F)(F)F)n1] | 154 | <5 | <5 | <5 | |
| 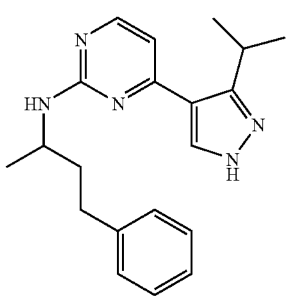 [SMILES: CC(CCc1ccccc1)Nc1nccc(-c2c[nH]nc2C(C)C)n1] | 155 | <1 | <5 | <5 | |
| 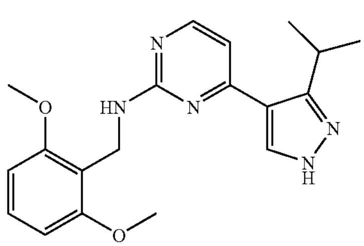 [SMILES: COc1cccc(OC)c1CNc1nccc(-c2c[nH]nc2C(C)C)n1] | 156 | <15 | 15 | 15 | <15 |

TABLE 2-continued
All values listed are IC50 numbers in umol-1.
| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbin h [umol l-1] |
|---|---|---|---|---|---|
| 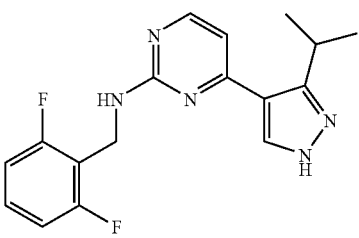 [SMILES: CC(C)c1n[nH]cc1-c1ccnc(NCc2c(F)cccc2F)n1] | 157 | <1 | <1 | <5 | |
| 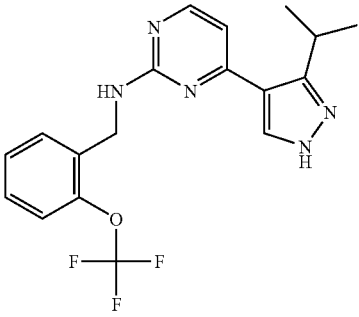 [SMILES: CC(C)c1n[nH]cc1-c1ccnc(NCc2ccccc2OC(F)(F)F)n1] | 158 | <15 | <5 | 15 | |
| 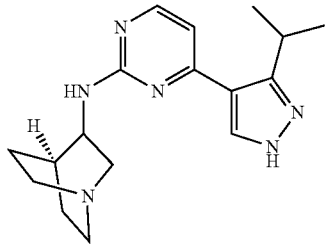 | 159 | <.05 | <.5 | <5 | <5 |
| 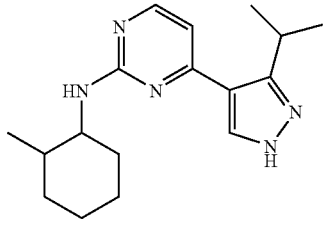 [SMILES: CC(C)c1n[nH]cc1-c1ccnc(NC2CCCCC2C)n1] | 160 | <.1 | <.5 | <1 | <5 |
| 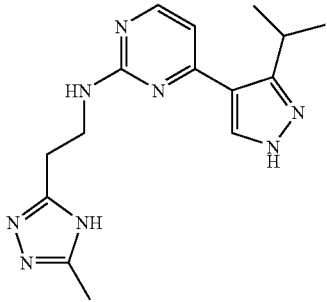 [SMILES: Cc1nnc(CCNc2nccc(-c3c[nH]nc3C(C)C)n2)[nH]1] | 161 | <.5 | <5 | <5 | |

TABLE 2-continued

All values listed are IC50 numbers in umol-1.

| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbin h [umol l-1] |
|---|---|---|---|---|---|
| 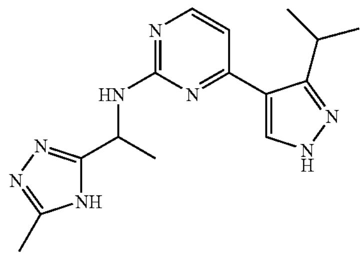 [SMILES: Cc1nnc(C(C)Nc2nccc(-c3c[nH]nc3C(C)C)n2)[nH]1] | 162 | <.5 | <10 | <15 | |
| 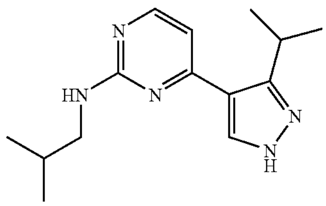 [SMILES: CC(C)CNc1nccc(-c2c[nH]nc2C(C)C)n1] | 163 | <.1 | <.5 | <.1 | <5 |
| 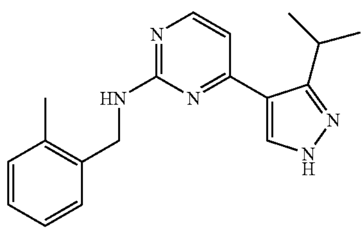 [SMILES: Cc1ccccc1CNc1nccc(-c2c[nH]nc2C(C)C)n1] | 164 | <.5 | <.5 | <1 | |
| 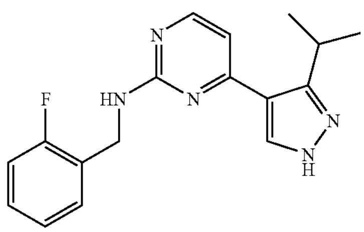 [SMILES: CC(C)c1n[nH]cc1-c1ccnc(NCc2ccccc2F)n1] | 165 | <1 | <.5 | <.5 | |
| 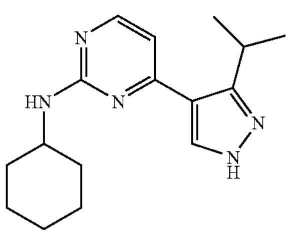 [SMILES: CC(C)c1n[nH]cc1-c1ccnc(NC2CCCCC2)n1] | 166 | <.05 | <.05 | <.05 | <1 |
| 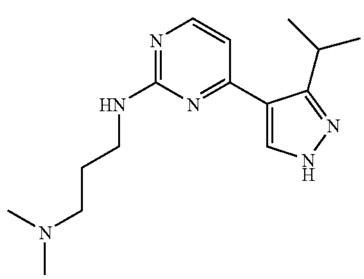 [SMILES: CC(C)c1n[nH]cc1-c1ccnc(NCCCN(C)C)n1] | 167 | <1 | <5 | <10 | |

TABLE 2-continued

All values listed are IC50 numbers in umol-1.

| Structure | Example Number | CDK4 HTRF/ IC50 [umol I-1] | hCDK1/B/ IC50 [umol I-1] | CDK2cyA IMAP/ IC50 [umol I-1] | p_pRb Cap EL/ IC50_ppRbin h [umol I-1] |
| --- | --- | --- | --- | --- | --- |
| (structure) | 168 | <.05 | <1 | <5 | |
| (structure) | 169 | <.05 | <5 | <1 | <5 |
| (structure) | 170 | <.05 | <.5 | <.5 | <5 |
| (structure) | 171 | <.05 | <.5 | <.5 | |
| (structure) | 172 | <.05 | <.5 | <.5 | |

TABLE 2-continued

All values listed are IC50 numbers in umol-1.

| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbinh [umol l-1] |
|---|---|---|---|---|---|
| (structure) | 173 | <.5 | <15 | 15 | |
| (structure) | 174 | <.05 | <1 | <1 | <5 |
| (structure) | 175 | <1 | <5 | <5 | |
| (structure) | 176 | <.05 | <.5 | <.5 | <1 |
| (structure) | 177 | <.05 | <5 | <.5 | <1 |
| (structure) | 178 | <5 | <10 | 15 | <15 |

TABLE 2-continued

All values listed are IC50 numbers in umol-1.

| Structure | Example Number | CDK4 HTRF/ IC50 [umol l-1] | hCDK1/B/ IC50 [umol l-1] | CDK2cyA IMAP/ IC50 [umol l-1] | p_pRb Cap EL/ IC50_ppRbinh [umol l-1] |
|---|---|---|---|---|---|
| 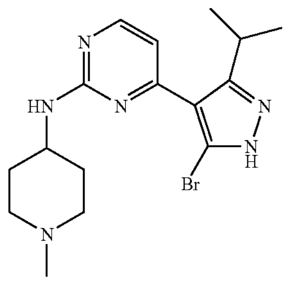 [SMILES: CC(C)c1n[nH]c(Br)c1-c1ccnc(NC2CCN(C)CC2)n1] | 179 | <.1 | <5 | <5 | <1 |
| 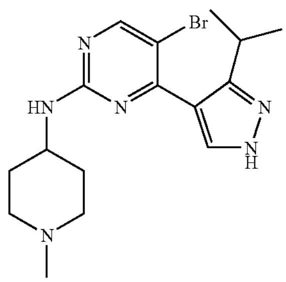 [SMILES: CC(C)c1n[nH]cc1-c1nc(NC2CCN(C)CC2)ncc1Br] | 180 | <1 | <5 | <5 | |
| 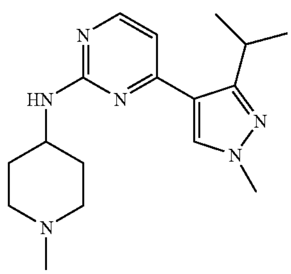 [SMILES: CC(C)c1nn(C)cc1-c1ccnc(NC2CCN(C)CC2)n1] | 181 | <.5 | <5 | <5 | |
| 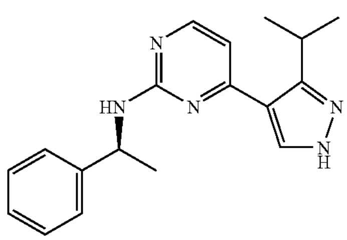 [SMILES: CC(C)c1n[nH]cc1-c1ccnc(N[C@@H](C)c2ccccc2)n1] | 182 | <10 | <5 | <10 | |
| 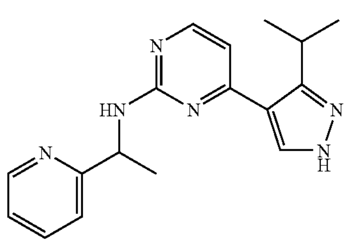 [SMILES: CC(C)c1n[nH]cc1-c1ccnc(NC(C)c2ccccn2)n1] | 183 | <.5 | <10 | <10 | |

TABLE 2-continued

All values listed are IC50 numbers in umol-1.

| Structure | Example Number | CDK4 HTRF/ IC50 [umol I-1] | hCDK1/B/ IC50 [umol I-1] | CDK2cyA IMAP/ IC50 [umol I-1] | p_pRb Cap EL/ IC50_ppRbin h [umol I-1] |
|---|---|---|---|---|---|
| 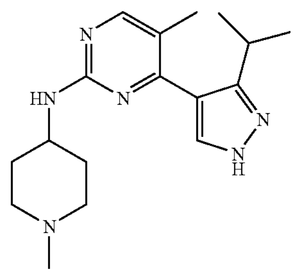 [SMILES: Cc1cnc(NC2CCN(C)CC2)nc1-c1c[nH]nc1C(C)C] | 184 | <.5 | <5 | <5 | |
| 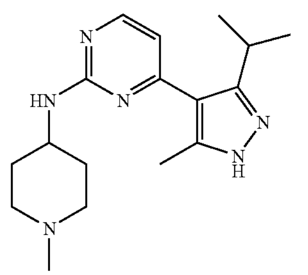 [SMILES: Cc1[nH]nc(C(C)C)c1-c1ccnc(NC2CCN(C)CC2)n1] | 185 | <5 | 15 | 15 | |
| 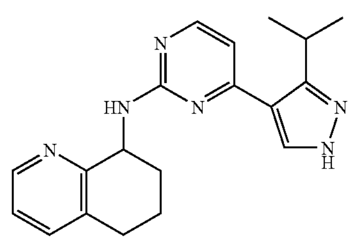 [SMILES: CC(C)c1n[nH]cc1-c1ccnc(NC2CCCc3cccnc32)n1] | 186 | <.5 | 15 | >15 | |
| 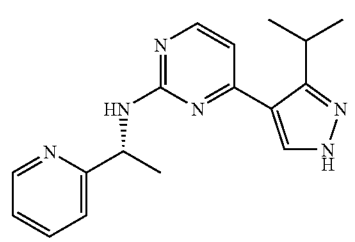 [SMILES: CC(C)c1n[nH]cc1-c1ccnc(N[C@H](C)c2ccccn2)n1] | 187 | <.1 | <5 | <5 | |
| 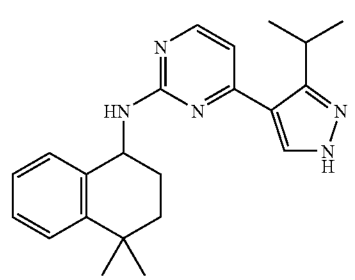 [SMILES: CC(C)c1n[nH]cc1-c1ccnc(NC2CCC(C)(C)c3ccccc32)n1] | 188 | <.1 | 15 | 15 | <5 |

TABLE 2-continued

All values listed are IC50 numbers in umol-1.

| Structure | Example Number | CDK4 HTRF/ IC50 [umol I-1] | hCDK1/B/ IC50 [umol I-1] | CDK2cyA IMAP/ IC50 [umol I-1] | p_pRb Cap EL/ IC50_ppRbinh [umol I-1] |
|---|---|---|---|---|---|
| (6-fluoro-indanyl-amino-pyrimidinyl isopropyl pyrazole) | 189 | <.1 | <.5 | <.5 | <1 |
| (5-chloro-indanyl-amino-pyrimidinyl isopropyl pyrazole) | 190 | <.5 | <5 | <.5 | <5 |
| (3,3-dimethyl-indanyl-amino-pyrimidinyl isopropyl pyrazole) | 191 | <.5 | <5 | <5 | |

Biological Activity p-pRb/S780 ELISA Cellular Assay

Maxisorp plates (Nunc 442404) are coated with 50 ul of 1 ug/mL total phospholated Retinoblast Protein (pRb) antibody (4H1 Cell Signaling 9309L) diluted in DPBS (Phosphate Buffered Saline) overnight at 4° C. The next day plates are blocked with Superblock in TBST (Pierce 37535) for one hour to overnight—changing block once during that time. Cells are plated at 50-60% confluency in a 96 well plate (Corning 3585) in 100 uL complete media (media containing fetal bovine serum (Gibco 1600-044), 2 mM L-Glutamine (Gibco 25030), and 1% Penicillin/Streptomycin (Gibco 15140-122) and grown overnight in a humidified chamber at 37° C. and 5% $CO_2$. Compounds (in DMSO) are diluted in media to create a 7 point dilution series of compound with concentrations ranging from 110 uM to 0.027 uM. 10 ul of the diluted compounds are added to the cells, with final concentrations on cells ranging from 10 uM to 0.002 uM. Cells are treated for 24 hrs in a humidified chamber at 37° C. and 5% $CO_2$. Following compound incubation, cells are lysed with 40 uL/well lysis buffer (50 mM Tris-HCL pH 7.5 (Invitrogen 15567-027), 120 mM NaCl (Promega V4221), 1 mM EDTA (Gibco 15575-038), 6 mM EGTA (Fisher 02783-100), 1% Nonidet P40 (Fluka R02771). Plates are placed on Titerplate shaker (Labline model 4625) for 5 minutes at 4° C. to lyse cells. After lysis, 10 ul of cell lysate and 50 ul 1×PBS/10% Superblock (Gibco 10010 and Pierce 37535) is added to each well of the precoated and blocked Maxisorp plate and allowed to bind at room temperature for 2 hours on Oribtron Rotator II (Boekel Industries Model 260250). Plates are then washed 3× with 1×TBST (Teknova T9201) using Biotek platewasher equipped with a Biostack. The final wash is not aspirated. The final wash is removed by flicking off and tapping plate on paper towels. ppRbS780 antibody (Cell Signaling 9307L) is diluted 1:1000 in 1×PBS/10% Superblock (Gibco 10010 and Pierce 37535) and 50 ul is added to each well. Plates are then incubated 1 hour on Oribtron Rotator II (Boekel Industries Model 260250). Plates are then washed as previously described. Goat anti-rabbit HRP (Promega W401B) is diluted 1:2500 1×PBS/10% Superblock (Gibco 10010 and Pierce 37535) and 50 ul is added to each well. Plates are then incubated 30 minutes on Oribtron Rotator II. Plates are then washed as previously described. 50 uL Ultra TMB ELISA (Pierce 34028) is then added to each well. Plates are incubated 5-20 minutes until blue color develops. 50 ul 2M Sulfuric acid (Mallinckrodt 2468-46) is then added to each well to stop the reaction. Absorbance at 450 nm for each plate is read on Spectramax Plus (Molecular Devices). The results of this assay are summarized in Tables 1 and 2.

BrdU Assay

Cell Proliferation ELISA BrdU (colorimetric) kit from Roche Diagnostic (Cat. #: 11647229001, 9115 Hague Road, Indianapolis, Ind. 50414) is used for this assay. Briefly, cells are plated in 96 well plates at 50-60% confluency in RMPI 1640 media. The next day, cells are treated with compounds at a desired concentration range and then incubated for 24 hrs in a humidified chamber at 37° C. and 5% $CO_2$. Following the protocol provided by the kit, cells are labeled with BrdU labeling agent for 2 hrs, and then fixed with 200 uL of FixDenat for 30 min at room temperature. 100 uL of anti-BrdU antibody is added to the cells and incubated for 2 hrs at room temperature. The cells are then washed three times with 200 uL/well of PBS, and then 100 uL of color developing solution is added per well. After 5-10 min incubation, the absorbance is read at 370 nM using Spectramax Plus (Molecular Devices). The results of this assay are summarized in Tables 1 and 2.

The above preferred embodiments are given to illustrate the scope and spirit of the present invention. The descriptions provided herein will make apparent to those skilled in the art other embodiments and examples. These other embodiments and examples are within the contemplation of the present invention. Therefore, the present invention should be limited only by the appended claims.

What is claimed is:

1. A compound of formula I:

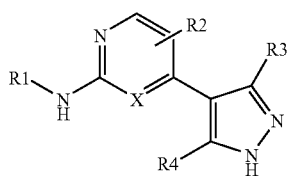

or a pharmaceutically acceptable salt, wherein $R^1$ is $C_{3-14}$-cycloalkyl, $C_{6-14}$aryl, a 3-14 membered cycloheteroalkyl group, $C_{1-6}$alkyl$C_{6-14}$aryl, or $C_{1-6}$alkyl $C_{3-14}$cycloalkyl, which may be unsubstituted or substituted with one or more of $C_{1-6}$-alkyl or $C_{6-14}$-aryl;

$R^2$ is H, $C_{1-6}$-alkyl, $C_{2-6}$-alkenyl, $C_{2-6}$-alkynyl, hydroxyl, or halo;

$R^3$ and $R^4$ are independently H, $C_{1-6}$-alkyl, or $C_{3-14}$-cycloalkyl; and X is N or $CR^{12}$ where $R^{11}$ and $R^{12}$ are independently H, halogen, or $C_{1-6}$-alkyl.

2. The compound of formula I or a pharmaceutically acceptable salt thereof according to claim 1 wherein one of $R^3$ and $R^4$ is H and the other of $R^3$ and $R^4$ is $C_{1-6}$-alkyl, or $C_{3-14}$-cycloalkyl.

3. The compound of formula I or a pharmaceutically acceptable salt thereof according to claim 1 wherein $R^4$ is H and $R^3$ is methyl, ethyl, or propyl.

4. The compound of formula I or a pharmaceutically acceptable salt thereof according to claim 1 wherein X is N or CH.

5. The compound of formula I or a pharmaceutically acceptable salt thereof according to claim 1 wherein X is N.

6. The compound of formula I or a pharmaceutically acceptable salt thereof according to claim 1 wherein $R^1$ is selected from:

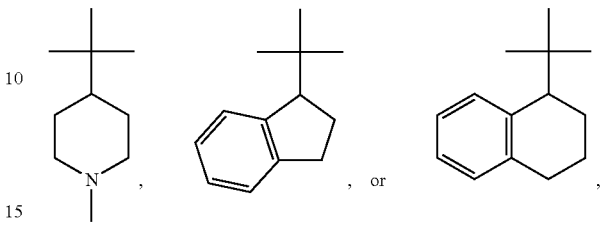

and
$R^3$ is methyl or isopropyl.

7. A pharmaceutical composition comprising a therapeutically effective amount of a compound of formula I or a pharmaceutically acceptable salt thereof according to claim 1.

8. The compound of formula I or a pharmaceutically acceptable salt thereof according to claim 1 wherein $R^3$ is isopropyl.

9. The compound of formula I or a pharmaceutically acceptable salt thereof according to claim 1 wherein $R^4$ is H; $R^3$ is methyl, ethyl, or propyl; and X is N.

10. The compound of formula I or a pharmaceutically acceptable salt thereof according to claim 1 wherein $R^1$ is selected from:

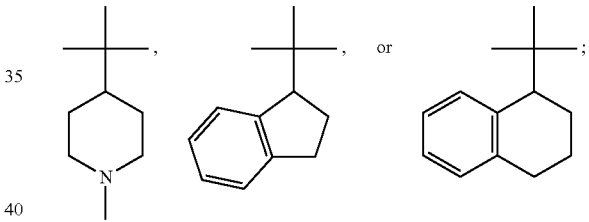

$R^3$ is methyl or isopropyl;
and X is N.

11. A method of treating a mammal suffering from cancer which comprises administering to said mammal in need of treatment a therapeutically effective amount of a compound of formula I according to claim 1, or a pharmaceutically acceptable salt thereof, wherein the cancer is breast cancer, genitourinary cancer, lung cancer, gastrointestinal cancer, epidermoid cancer, multiple myeloma, melanoma, ovarian cancer, pancreas cancer, neuroblastoma, nose cancer, head and neck cancer, or bladder cancer.

* * * * *